US008361964B2

(12) United States Patent
Peri et al.

(10) Patent No.: US 8,361,964 B2
(45) Date of Patent: Jan. 29, 2013

(54) GROWTH HORMONE RELEASING FACTOR (GRF) ANALOGS AND USES THEREOF

(75) Inventors: Krishna G. Peri, Montreal (CA); Abdelkrim Habi, Pierrefonds (CA)

(73) Assignee: Theratechnologies Inc., Montreal (CA)

( * ) Notice: Subject to any disclaimer, the term of this patent is extended or adjusted under 35 U.S.C. 154(b) by 0 days.

(21) Appl. No.: 13/448,660

(22) Filed: Apr. 17, 2012

(65) Prior Publication Data

US 2012/0270784 A1 Oct. 25, 2012

Related U.S. Application Data

(60) Provisional application No. 61/477,775, filed on Apr. 21, 2011.

(51) Int. Cl.
*A61K 38/25* (2006.01)

(52) U.S. Cl. ........ 514/11.2; 530/324; 530/300; 514/1.1; 514/7.6; 514/9.7; 514/21.3

(58) Field of Classification Search .................. None
See application file for complete search history.

(56) References Cited

U.S. PATENT DOCUMENTS

| | | | |
|---|---|---|---|
| 4,518,586 A | 5/1985 | Rivier et al. | |
| 4,617,149 A | 10/1986 | DiMarchi et al. | |
| 4,622,312 A | 11/1986 | Felix et al. | |
| 4,734,399 A * | 3/1988 | Felix et al. ................. | 514/11.2 |
| 4,801,456 A | 1/1989 | Drengler | |
| 5,262,519 A | 11/1993 | Rivier et al. | |
| 5,846,936 A | 12/1998 | Felix et al. | |
| 5,847,066 A | 12/1998 | Coy et al. | |
| 5,939,386 A | 8/1999 | Ibea et al. | |
| 6,528,485 B1 | 3/2003 | Veronese et al. | |
| 7,026,281 B1 | 4/2006 | Schally et al. | |
| 7,256,258 B2 | 8/2007 | Piquet et al. | |
| 7,268,113 B2 | 9/2007 | Bridon et al. | |
| 7,452,865 B2 | 11/2008 | Schally et al. | |
| 2006/0128615 A1 | 6/2006 | Gaudreau | |
| 2009/0023646 A1 | 1/2009 | Gaudreau | |
| 2009/0088380 A1 | 4/2009 | Gaudreau | |
| 2010/0041098 A1 | 2/2010 | Steward | |
| 2010/0267636 A1 | 10/2010 | Marsolais | |
| 2011/0021429 A1 | 1/2011 | Gaudreau et al. | |

FOREIGN PATENT DOCUMENTS

| | | |
|---|---|---|
| WO | WO2004105789 | 9/2004 |
| WO | WO2005037307 | 4/2005 |
| WO | WO2006042408 | 4/2006 |
| WO | WO2009009727 | 1/2009 |

OTHER PUBLICATIONS

Gaudreau G. et al; "Affinity of human growth hormone releasing factor (1-29) NH2 analogues for GRF binding sites in rat adenopituitary." Journal of Medicinal Chemistry (1992) 35(10) p. 1864-1869.*

Cervini, L. A. et al; "Human growth hormone releasing hormone hGHRH(1-29)-NH2: Systematic structure-activity relationship studies." Journal of Medicinal Chemistry (1998) 41(5) p. 717-727.*

Jette et al., Human Growth Hormone-Releasing Factor (hGRF)1-29-Albumin Bioconjugates Activate the GRF Receptor on the Anterior Pituitary in Rats: Identification of CJC-1295 as a Long-Lasting GRF Analog, Endocrinology 146:3052-3058 (2005).

International Search Report and Written Opinion of the International Searching Authority issued in connection with counterpart international application, PCT/CA2012/050242 and mailed Jul. 4, 2012 (12 pages).

Frohman L.A., et al., Growth Hormone-Releasing Hormone, Endocrine Reviews, 1986, 7:223-253.

Frohman L.A., et al., Rapid Enzymatic Degradation of Growth Hormone-releasing Hormone by Plasma in Vitro and in Vivo to a Biologically Inactive Product Cleaved at the NH2 Terminus, J. Clin. Invest., 1986, 78:906-913.

Lance V.A., et al., Super-Active Analogs of Growth Hormone-Releasing Factor (1-29)-Amide, Biochemical and Biophysical Research Communications, 1984, 119:265-272.

Khorram O., et al., Use of Growth Hormone and Growth Hormone Secretagogues in Aging: Help or Harm, Clinical Obstetrics and Gynecology, 2001, 44:893-901.

Thorner M., et al., Once Daily Subcutaneous Growth Hormone-Releasing Hormone Therapy Accelerates Growth in Growth Hormone-Deficient Children during the First Year of Therapy, Journal of Clinical Endocrinology and Metabolism, 1996, 81:1189-1196.

* cited by examiner

*Primary Examiner* — Anish Gupta
*Assistant Examiner* — Fred Reynolds
(74) *Attorney, Agent, or Firm* — Fish & Richardson P.C.

(57) ABSTRACT

Novel GRF analogs having GRF activity are described herein, as well as uses thereof for example as a GRF receptor agonist, e.g., to induce growth hormone secretion in a subject or biological system.

30 Claims, No Drawings

SEQUENCE LISTING

<160> NUMBER OF SEQ ID NOS: 46

<210> SEQ ID NO 1
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is Tyr or His
<220> FEATURE:
<221> NAME/KEY: MISC_FEATURE
<222> LOCATION: (2)..(2)
<223> OTHER INFORMATION: Xaa at position 2 is Ala, D-Ala, Ser, Leu,
      alpha-aminoisobutyric acid (Aib), Val or Gly
<220> FEATURE:
<221> NAME/KEY: MISC_FEATURE
<222> LOCATION: (8)..(8)
<223> OTHER INFORMATION: Xaa at position 8 is Asn, Asp, Ala, Gln, Ser or
      Aib
<220> FEATURE:
<221> NAME/KEY: MISC_FEATURE
<222> LOCATION: (9)..(9)
<223> OTHER INFORMATION: Xaa at position 9 is Ser, Asp or Ala
<220> FEATURE:
<221> NAME/KEY: MISC_FEATURE
<222> LOCATION: (11)..(11)
<223> OTHER INFORMATION: Xaa at position 11 is Arg or L-Homoarginine
<220> FEATURE:
<221> NAME/KEY: MISC_FEATURE
<222> LOCATION: (12)..(12)
<223> OTHER INFORMATION: Xaa at position 12 is Lys, L-Ornithine or
      L-Homoarginine
<220> FEATURE:
<221> NAME/KEY: MISC_FEATURE
<222> LOCATION: (13)..(13)
<223> OTHER INFORMATION: Xaa at position 13 is Val or Ile
<220> FEATURE:
<221> NAME/KEY: MISC_FEATURE
<222> LOCATION: (15)..(15)
<223> OTHER INFORMATION: Xaa at position 15 is Gly or Ala;
<220> FEATURE:
<221> NAME/KEY: MISC_FEATURE
<222> LOCATION: (18)..(18)
<223> OTHER INFORMATION: Xaa at position 18 is Lys, L-Ornithine,
      L-2,4-diaminobutyric acid, L-2,3-diaminopropionic acid or Ser;
<220> FEATURE:
<221> NAME/KEY: MISC_FEATURE
<222> LOCATION: (18)..(18)
<223> OTHER INFORMATION: If Xaa at position 18 is Ser, the Xaa at
      positions 27 to 32 or 27 to 33 are present;
<220> FEATURE:
<221> NAME/KEY: MISC_FEATURE
<222> LOCATION: (19)..(19)
<223> OTHER INFORMATION: Xaa at position 19 is Ala or Leu;
<220> FEATURE:
<221> NAME/KEY: MISC_FEATURE
<222> LOCATION: (22)..(22)
<223> OTHER INFORMATION: Xaa at position 22 is Asp or Glu;
<220> FEATURE:
<221> NAME/KEY: MISC_FEATURE
<222> LOCATION: (23)..(23)
<223> OTHER INFORMATION: Xaa at position 23 is Ile or Leu;
<220> FEATURE:
<221> NAME/KEY: MISC_FEATURE
<222> LOCATION: (24)..(24)
<223> OTHER INFORMATION: Xaa at position 24 is Met, Ile, Nle or Leu;
<220> FEATURE:
<221> NAME/KEY: MISC_FEATURE
<222> LOCATION: (25)..(25)
<223> OTHER INFORMATION: Xaa at position 25 is Ser, Asn, Aib or Ala;
<220> FEATURE:
<221> NAME/KEY: MISC_FEATURE
<222> LOCATION: (26)..(26)
<223> OTHER INFORMATION: Xaa at position 26 is Arg, D-Arg,

```
            L-Homoarginine or Lys;
<220> FEATURE:
<221> NAME/KEY: MISC_FEATURE
<222> LOCATION: (27)..(27)
<223> OTHER INFORMATION: Xaa at position 27 is Ala or is absent;
<220> FEATURE:
<221> NAME/KEY: MISC_FEATURE
<222> LOCATION: (28)..(28)
<223> OTHER INFORMATION: Xaa at position 28 is Ala or is absent;
<220> FEATURE:
<221> NAME/KEY: MISC_FEATURE
<222> LOCATION: (29)..(29)
<223> OTHER INFORMATION: Xaa at position 29 is Arg or is absent;
<220> FEATURE:
<221> NAME/KEY: MISC_FEATURE
<222> LOCATION: (30)..(30)
<223> OTHER INFORMATION: Xaa at position 30 is Ala or is absent;
<220> FEATURE:
<221> NAME/KEY: MISC_FEATURE
<222> LOCATION: (31)..(31)
<223> OTHER INFORMATION: Xaa at position 31 is Ala or is absent;
<220> FEATURE:
<221> NAME/KEY: MISC_FEATURE
<222> LOCATION: (32)..(32)
<223> OTHER INFORMATION: Xaa at position 32 is Arg or is absent;
<220> FEATURE:
<221> NAME/KEY: MISC_FEATURE
<222> LOCATION: (33)..(33)
<223> OTHER INFORMATION: Xaa at position 33 is HoSer or is absent;

<400> SEQUENCE: 1

Xaa Xaa Asp Ala Ile Phe Thr Xaa Xaa Tyr Xaa Xaa Xaa Leu Xaa Gln
1               5                   10                  15

Leu Xaa Xaa Arg Gln Xaa Xaa Xaa Xaa Xaa Xaa Xaa Xaa Xaa Xaa Xaa
            20                  25                  30

Xaa

<210> SEQ ID NO 2
<211> LENGTH: 26
<212> TYPE: PRT
<213> ORGANISM: Artificial Sequence
<220> FEATURE:
<223> OTHER INFORMATION: Synthetic peptide

<400> SEQUENCE: 2

Tyr Ala Asp Ala Ile Phe Thr Asp Ser Tyr Arg Lys Val Leu Ala Gln
1               5                   10                  15

Leu Lys Ala Arg Gln Asp Ile Leu Ala Arg
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (26)..(26)
<223> OTHER INFORMATION: Xaa at position 26 is D-Arg

<400> SEQUENCE: 3

Tyr Xaa Asp Ala Ile Phe Thr Asp Ser Tyr Arg Lys Val Leu Ala Gln
1               5                   10                  15

Leu Lys Ala Arg Gln Asp Ile Leu Ser Xaa
            20                  25
```

-continued

```
<210> SEQ ID NO 4
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (25)..(25)
<223> OTHER INFORMATION: Aib

<400> SEQUENCE: 4

Tyr Xaa Asp Ala Ile Phe Thr Asp Ser Tyr Arg Lys Val Leu Ala Gln
1               5                   10                  15

Leu Lys Ala Arg Gln Asp Ile Leu Xaa Arg
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (18)..(18)
<223> OTHER INFORMATION: Orn
<220> FEATURE:
<221> NAME/KEY: MISC_FEATURE
<222> LOCATION: (26)..(26)
<223> OTHER INFORMATION: Xaa at position 26 is D-Arg

<400> SEQUENCE: 5

Tyr Xaa Asp Ala Ile Phe Thr Asp Ser Tyr Arg Lys Val Leu Ala Gln
1               5                   10                  15

Leu Xaa Ala Arg Gln Asp Ile Leu Ser Xaa
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: Xaa at position 18 is L-Ornithine
<220> FEATURE:
<221> NAME/KEY: MISC_FEATURE
<222> LOCATION: (26)..(26)
<223> OTHER INFORMATION: Xaa at position 26 is D-Arg

<400> SEQUENCE: 6

Tyr Ala Asp Ala Ile Phe Thr Asp Ser Tyr Arg Lys Val Leu Ala Gln
1               5                   10                  15

Leu Xaa Ala Arg Gln Asp Ile Leu Ser Xaa
            20                  25

<210> SEQ ID NO 7
<211> LENGTH: 26
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala;
<220> FEATURE:
<221> NAME/KEY: MISC_FEATURE
<222> LOCATION: (26)..(26)
<223> OTHER INFORMATION: Xaa at position 26 is D-Arg;

<400> SEQUENCE: 7

Tyr Xaa Asp Ala Ile Phe Thr Asp Ser Tyr Arg Lys Val Leu Ala Gln
1               5                   10                  15

Leu Lys Ala Arg Gln Asp Ile Leu Ser Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic peptide

<400> SEQUENCE: 8

Tyr Ala Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg
            20                  25

<210> SEQ ID NO 9
<211> LENGTH: 32
<212> TYPE: PRT
<213> ORGANISM: Artificial Sequence
<220> FEATURE:
<223> OTHER INFORMATION: Synthetic peptide

<400> SEQUENCE: 9

Tyr Ala Asp Ala Ile Phe Thr Asp Ser Tyr Arg Lys Val Leu Ala Gln
1               5                   10                  15

Leu Ser Ala Arg Gln Asp Ile Leu Ala Arg Ala Ala Arg Ala Ala Arg
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala

<400> SEQUENCE: 10

Tyr Xaa Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic peptide
<220> FEATURE:
```

-continued

```
<221> NAME/KEY: MISC_FEATURE
<222> LOCATION: (2)..(2)
<223> OTHER INFORMATION: Xaa at position 2 is D-Ala

<400> SEQUENCE: 11

Tyr Xaa Asp Ala Ile Phe Thr Asp Ser Tyr Arg Lys Val Leu Ala Gln
1               5                   10                  15

Leu Lys Leu Arg Gln Asp Ile Leu Ala Arg Ala Ala Arg Ala Ala Arg
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala

<400> SEQUENCE: 12

Tyr Xaa Asp Ala Ile Phe Thr Asp Ser Tyr Arg Lys Val Leu Ala Gln
1               5                   10                  15

Leu Lys Ala Arg Gln Asp Leu Leu Ala Arg Ala Ala Arg Ala Ala Arg
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Synthetic peptide

<400> SEQUENCE: 13

Tyr Ala Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic peptide

<400> SEQUENCE: 14

Tyr Ala Asp Ala Ile Phe Thr Asp Ser Tyr Arg Lys Val Leu Ala Gln
1               5                   10                  15

Leu Lys Ala Arg Gln Asp Leu Leu Ala Arg Ala Ala Arg Ala Ala Arg
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic peptide

<400> SEQUENCE: 15

Tyr Ser Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30
```

```
<210> SEQ ID NO 16
<211> LENGTH: 32
<212> TYPE: PRT
<213> ORGANISM: Artificial Sequence
<220> FEATURE:
<223> OTHER INFORMATION: Synthetic peptide

<400> SEQUENCE: 16

Tyr Gly Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Synthetic peptide

<400> SEQUENCE: 17

Tyr Leu Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 18
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (33)..(33)
<223> OTHER INFORMATION: Xaa at position 33 is L-Homoserine

<400> SEQUENCE: 18

Tyr Gly Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

Xaa

<210> SEQ ID NO 19
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MISC_FEATURE
<222> LOCATION: (33)..(33)
<223> OTHER INFORMATION: Xaa at position 33 is L-Homoserine

<400> SEQUENCE: 19

Tyr Xaa Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

Xaa
```

-continued

```
<210> SEQ ID NO 20
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (26)..(26)
<223> OTHER INFORMATION: AMIDATION

<400> SEQUENCE: 20

Tyr Ala Asp Ala Ile Phe Thr Asp Ser Tyr Arg Lys Val Leu Ala Gln
1               5                   10                  15

Leu Lys Ala Arg Gln Asp Ile Leu Ala Arg
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: MOD_RES
<222> LOCATION: (26)..(26)
<223> OTHER INFORMATION: AMIDATION
<220> FEATURE:
<221> NAME/KEY: misc_feature
<222> LOCATION: (26)..(26)
<223> OTHER INFORMATION: Xaa at position 26 is D-Arg

<400> SEQUENCE: 21

Tyr Xaa Asp Ala Ile Phe Thr Asp Ser Tyr Arg Lys Val Leu Ala Gln
1               5                   10                  15

Leu Lys Ala Arg Gln Asp Ile Leu Ser Xaa
            20                  25

<210> SEQ ID NO 22
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (26)..(26)
<223> OTHER INFORMATION: AMIDATION

<400> SEQUENCE: 22

Tyr Xaa Asp Ala Ile Phe Thr Asp Ser Tyr Arg Lys Val Leu Ala Gln
1               5                   10                  15

Leu Lys Ala Arg Gln Asp Ile Leu Xaa Arg
            20                  25
```

```
<210> SEQ ID NO 23
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (18)..(18)
<223> OTHER INFORMATION: Orn
<220> FEATURE:
<221> NAME/KEY: MISC_FEATURE
<222> LOCATION: (26)..(26)
<223> OTHER INFORMATION: Xaa at position 26 is D-Arg
<220> FEATURE:
<221> NAME/KEY: MOD_RES
<222> LOCATION: (26)..(26)
<223> OTHER INFORMATION: AMIDATION

<400> SEQUENCE: 23

Tyr Xaa Asp Ala Ile Phe Thr Asp Ser Tyr Arg Lys Val Leu Ala Gln
1               5                   10                  15

Leu Xaa Ala Arg Gln Asp Ile Leu Ser Xaa
            20                  25

<210> SEQ ID NO 24
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (18)..(18)
<223> OTHER INFORMATION: Orn
<220> FEATURE:
<221> NAME/KEY: MISC_FEATURE
<222> LOCATION: (26)..(26)
<223> OTHER INFORMATION: Xaa at position 26 is D-Arg

<400> SEQUENCE: 24

Tyr Ala Asp Ala Ile Phe Thr Asp Ser Tyr Arg Lys Val Leu Ala Gln
1               5                   10                  15

Leu Xaa Ala Arg Gln Asp Ile Leu Ser Xaa
            20                  25

<210> SEQ ID NO 25
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala;
<220> FEATURE:
<221> NAME/KEY: MOD_RES
<222> LOCATION: (26)..(26)
<223> OTHER INFORMATION: AMIDATION
<220> FEATURE:
<221> NAME/KEY: MISC_FEATURE
<222> LOCATION: (26)..(26)
```

```
<223> OTHER INFORMATION: Xaa at position 26 is D-Arg;

<400> SEQUENCE: 25

Tyr Xaa Asp Ala Ile Phe Thr Asp Ser Tyr Arg Lys Val Leu Ala Gln
1               5                   10                  15

Leu Lys Ala Arg Gln Asp Ile Leu Ser Xaa
            20                  25

<210> SEQ ID NO 26
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (29)..(29)
<223> OTHER INFORMATION: AMIDATION

<400> SEQUENCE: 26

Tyr Ala Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg
            20                  25

<210> SEQ ID NO 27
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (32)..(32)
<223> OTHER INFORMATION: AMIDATION

<400> SEQUENCE: 27

Tyr Ala Asp Ala Ile Phe Thr Asp Ser Tyr Arg Lys Val Leu Ala Gln
1               5                   10                  15

Leu Ser Ala Arg Gln Asp Ile Leu Ala Arg Ala Ala Arg Ala Ala Arg
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (32)..(32)
<223> OTHER INFORMATION: AMIDATION

<400> SEQUENCE: 28

Tyr Xaa Asp Ala Ile Phe Thr Asp Ser Tyr Arg Lys Val Leu Ala Gln
1               5                   10                  15
```

```
Leu Lys Ala Arg Gln Asp Ile Leu Ala Arg Ala Ala Arg Ala Ala Arg
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (32)..(32)
<223> OTHER INFORMATION: AMIDATION

<400> SEQUENCE: 29

Tyr Xaa Asp Ala Ile Phe Thr Asp Ser Tyr Arg Lys Val Leu Ala Gln
1               5                   10                  15

Leu Lys Leu Arg Gln Asp Ile Leu Ala Arg Ala Ala Arg Ala Ala Arg
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (32)..(32)
<223> OTHER INFORMATION: AMIDATION

<400> SEQUENCE: 30

Tyr Xaa Asp Ala Ile Phe Thr Asp Ser Tyr Arg Lys Val Leu Ala Gln
1               5                   10                  15

Leu Lys Ala Arg Gln Asp Leu Leu Ala Arg Ala Ala Arg Ala Ala Arg
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (32)..(32)
<223> OTHER INFORMATION: AMIDATION

<400> SEQUENCE: 31

Tyr Ala Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 32
<211> LENGTH: 32
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (32)..(32)
<223> OTHER INFORMATION: AMIDATION

<400> SEQUENCE: 32

Tyr Ala Asp Ala Ile Phe Thr Asp Ser Tyr Arg Lys Val Leu Ala Gln
1               5                   10                  15

Leu Lys Ala Arg Gln Asp Leu Leu Ala Arg Ala Ala Arg Ala Ala Arg
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (32)..(32)
<223> OTHER INFORMATION: AMIDATION

<400> SEQUENCE: 33

Tyr Ser Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (32)..(32)
<223> OTHER INFORMATION: AMIDATION

<400> SEQUENCE: 34

Tyr Gly Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (32)..(32)
<223> OTHER INFORMATION: AMIDATION

<400> SEQUENCE: 35

Tyr Leu Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
```

```
                20                  25                  30

<210> SEQ ID NO 36
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (33)..(33)
<223> OTHER INFORMATION: Xaa at position 33 is L-Homoserine
<220> FEATURE:
<221> NAME/KEY: MOD_RES
<222> LOCATION: (33)..(33)
<223> OTHER INFORMATION: AMIDATION

<400> SEQUENCE: 36

Tyr Gly Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

Xaa

<210> SEQ ID NO 37
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (33)..(33)
<223> OTHER INFORMATION: AMIDATION
<220> FEATURE:
<221> NAME/KEY: MISC_FEATURE
<222> LOCATION: (33)..(33)
<223> OTHER INFORMATION: Xaa at position 33 is L-Homoserine

<400> SEQUENCE: 37

Tyr Xaa Asp Ala Ile Phe Thr Asp Ser Tyr Arg Lys Val Leu Ala Gln
1               5                   10                  15

Leu Lys Ala Arg Gln Asp Ile Leu Ala Arg Ala Ala Arg Ala Ala Arg
            20                  25                  30

Xaa

<210> SEQ ID NO 38
<211> LENGTH: 44
<212> TYPE: PRT
<213> ORGANISM: Homo sapiens

<400> SEQUENCE: 38

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln
            20                  25                  30

Gly Glu Ser Asn Glu Arg Gly Ala Arg Ala Arg Leu
        35                  40

<210> SEQ ID NO 39
<211> LENGTH: 29
<212> TYPE: PRT
<213> ORGANISM: Homo sapiens
```

<400> SEQUENCE: 39

Tyr Ala Asp Ala Ile Phe Thr Asn Ser Tyr Arg Lys Val Leu Gly Gln
1               5                   10                  15
Leu Ser Ala Arg Lys Leu Leu Gln Asp Ile Met Ser Arg
            20                  25

<210> SEQ ID NO 40
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is any amino acid
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (8)..(8)
<223> OTHER INFORMATION: Xaa at position 8 is any amino acid
<220> FEATURE:
<221> NAME/KEY: MISC_FEATURE
<222> LOCATION: (9)..(9)
<223> OTHER INFORMATION: Xaa at position 9 is any amino acid
<220> FEATURE:
<221> NAME/KEY: MISC_FEATURE
<222> LOCATION: (11)..(11)
<223> OTHER INFORMATION: Xaa at position 11 is any amino acid
<220> FEATURE:
<221> NAME/KEY: MISC_FEATURE
<222> LOCATION: (12)..(12)
<223> OTHER INFORMATION: Xaa at position 12 is any amino acid
<220> FEATURE:
<221> NAME/KEY: MISC_FEATURE
<222> LOCATION: (13)..(13)
<223> OTHER INFORMATION: Xaa at position 13 is any amino acid
<220> FEATURE:
<221> NAME/KEY: MISC_FEATURE
<222> LOCATION: (15)..(15)
<223> OTHER INFORMATION: Xaa at position 15 is any amino acid
<220> FEATURE:
<221> NAME/KEY: MISC_FEATURE
<222> LOCATION: (18)..(18)
<223> OTHER INFORMATION: Xaa at position 18 is any amino acid
<220> FEATURE:
<221> NAME/KEY: MISC_FEATURE
<222> LOCATION: (18)..(18)
<223> OTHER INFORMATION: If Xaa at position 18 is Ser, the Xaa at
    positions 27 to 32 or 27 to 33 are present;
<220> FEATURE:
<221> NAME/KEY: MISC_FEATURE
<222> LOCATION: (19)..(19)
<223> OTHER INFORMATION: Xaa at position 19 is any amino acid;
<220> FEATURE:
<221> NAME/KEY: MISC_FEATURE
<222> LOCATION: (22)..(22)
<223> OTHER INFORMATION: Xaa at position 22 is any amino acid;
<220> FEATURE:
<221> NAME/KEY: MISC_FEATURE
<222> LOCATION: (23)..(23)
<223> OTHER INFORMATION: Xaa at position 23 is any amino acid;
<220> FEATURE:
<221> NAME/KEY: MISC_FEATURE
<222> LOCATION: (24)..(24)
<223> OTHER INFORMATION: Xaa at position 24 is any amino acid;
<220> FEATURE:
<221> NAME/KEY: MISC_FEATURE
<222> LOCATION: (25)..(25)
<223> OTHER INFORMATION: Xaa at position 25 is any amino acid;
<220> FEATURE:
<221> NAME/KEY: MISC_FEATURE
<222> LOCATION: (26)..(26)

```
<223> OTHER INFORMATION: Xaa at position 26 is any amino acid;
<220> FEATURE:
<221> NAME/KEY: MISC_FEATURE
<222> LOCATION: (27)..(27)
<223> OTHER INFORMATION: Xaa at position 27 is any amino acid or is
      absent;
<220> FEATURE:
<221> NAME/KEY: MISC_FEATURE
<222> LOCATION: (28)..(28)
<223> OTHER INFORMATION: Xaa at position 28 is any amino acid or is
      absent;
<220> FEATURE:
<221> NAME/KEY: MISC_FEATURE
<222> LOCATION: (29)..(29)
<223> OTHER INFORMATION: Xaa at position 29 is any amino acid or is
      absent;
<220> FEATURE:
<221> NAME/KEY: MISC_FEATURE
<222> LOCATION: (30)..(30)
<223> OTHER INFORMATION: Xaa at position 30 is any amino acid or is
      absent;
<220> FEATURE:
<221> NAME/KEY: MISC_FEATURE
<222> LOCATION: (31)..(31)
<223> OTHER INFORMATION: Xaa at position 31 is any amino acid or is
      absent;
<220> FEATURE:
<221> NAME/KEY: MISC_FEATURE
<222> LOCATION: (32)..(32)
<223> OTHER INFORMATION: Xaa at position 32 is any amino acid or is
      absent;
<220> FEATURE:
<221> NAME/KEY: MISC_FEATURE
<222> LOCATION: (33)..(33)
<223> OTHER INFORMATION: Xaa at position 33 is any amino acid or is
      absent;

<400> SEQUENCE: 40

Xaa Xaa Asp Ala Ile Phe Thr Xaa Xaa Tyr Xaa Xaa Xaa Leu Xaa Gln
1               5                   10                  15

Leu Xaa Xaa Arg Gln Xaa Xaa Xaa Xaa Xaa Xaa Xaa Xaa Xaa Xaa Xaa
                20                  25                  30

Xaa

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide

<400> SEQUENCE: 41

Ala Ala Arg Ala Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa at position 7 is L-Homoserine

<400> SEQUENCE: 42

Ala Ala Arg Ala Ala Arg Xaa
1               5

<210> SEQ ID NO 43
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (29)..(29)
<223> OTHER INFORMATION: AMIDATION

<400> SEQUENCE: 43

Tyr Ala Asp Ala Ile Phe Thr Asp Ser Tyr Arg Lys Val Leu Ala Gln
1               5                   10                  15

Leu Ser Ala Arg Lys Leu Leu Gln Asp Ile Leu Ser Arg
            20                  25

<210> SEQ ID NO 44
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (26)..(26)
<223> OTHER INFORMATION: AMIDATION

<400> SEQUENCE: 44

Tyr Ala Asp Ala Ile Phe Thr Asp Ser Tyr Arg Lys Val Leu Ala Gln
1               5                   10                  15

Leu Ser Ala Arg Gln Asp Ile Met Ser Arg
            20                  25

<210> SEQ ID NO 45
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Tyr residue is linked to a trans-3-hexenoyl
      moiety
<220> FEATURE:
<221> NAME/KEY: MOD_RES
<222> LOCATION: (26)..(26)
<223> OTHER INFORMATION: AMIDATION

<400> SEQUENCE: 45

Tyr Ala Asp Ala Ile Phe Thr Asp Ser Tyr Arg Lys Val Leu Ala Gln
1               5                   10                  15

Leu Ser Ala Arg Gln Asp Ile Leu Ala Arg
            20                  25

<210> SEQ ID NO 46
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Tyr residue is linked to a trans-3-hexenoyl
      moiety
<220> FEATURE:
<221> NAME/KEY: MISC_FEATURE
<222> LOCATION: (26)..(26)
<223> OTHER INFORMATION: Xaa at position 26 is D-Arg
<220> FEATURE:
<221> NAME/KEY: MOD_RES
<222> LOCATION: (26)..(26)
<223> OTHER INFORMATION: AMIDATION

<400> SEQUENCE: 46

Tyr Ala Asp Ala Ile Phe Thr Asp Ser Tyr Arg Lys Val Leu Ala Gln
 1               5                  10                  15

Leu Ser Ala Arg Gln Asp Ile Leu Ser Xaa
            20                  25
```

GROWTH HORMONE RELEASING FACTOR (GRF) ANALOGS AND USES THEREOF

CROSS REFERENCE TO RELATED APPLICATIONS

This application claims the benefit of U.S. provisional application No. 61/477,775, filed on Apr. 21, 2011, which is incorporated herein by reference in its entirety.

FIELD OF THE INVENTION

The present invention generally relates to agonists of the growth hormone releasing factor (GRF) receptor, and uses thereof. In particular, the present invention relates to GRF analogs, and uses thereof.

REFERENCE TO SEQUENCE LISTING

Pursuant to 37 C.F.R. 1.821(c), a sequence listing is submitted herewith as an ASCII compliant text file named "Sequence_Listing.txt" that was created on Apr. 17, 2012, and having a size of 26,866 bytes. The content of the aforementioned file named "Sequence Listing.txt" is hereby incorporated by reference in its entirety.

BACKGROUND OF THE INVENTION

Growth hormone (GH) is produced in somatotroph cells of the anterior pituitary gland of mammals and secreted throughout life. It is mainly controlled in the brain by two hypothalamic peptides: GRF, which stimulates its secretion and synthesis; and somatostatin, which inhibits them. A number of peripheral factors regulate GH secretion. Among them, insulin-like growth factor-1 (IGF-1) represents an important one as it is produced by the liver in response to GH and acts on the hypothalamus to exert a negative feedback on GH secretion.

The decrease of GH secretion with age, demonstrated in humans and animals, favors a metabolic shift towards catabolism which initiates or participates in the aging of an organism. Loss of muscle mass, accumulation of adipose tissue, bone demineralization, and loss of tissue regeneration capacity after injury, which are observed in the elderly, correlate with the decrease in the secretion of GH.

GH is thus a physiological anabolic agent that is involved in the linear growth of children and which controls protein metabolism in adults.

GRF (also referred to as GH releasing hormone or GHRH) is a 44 amino acid peptide secreted by the hypothalamus that regulates the expression, synthesis and release of GH from the somatotroph cells of the anterior pituitary (Frohman L A et al. *Endocrine Reviews* 1986, 7: 223-253). A peptide consisting of the first 29 amino acids of human GRF (hGRF$_{(1-29)}$; sermorelin) retains the biological activity of the full-length peptide (Lance, V. A. et al., *Biochemical and Biophysical Research Communications* 1984, 119: 265-272) and has been used clinically for the treatment of GH deficiency in children (Thorner, M. et al., *Journal of Clinical Endocrinology and Metabolism* 1996, 81: 1189-1196). More recently, the potential of GRF to reverse the age-related decline in the function of the somatotrophic GH-insulin-like growth factor (IGF)-I axis has been evaluated (Khorram, O. et al., *Clinical Obstetrics and Gynecology* 2001, 44: 893-901).

A pharmaceutical preparation of hGRF$_{(1-29)}$ has been available for clinical use (Geref®, Laboratoires Serono S.A.). However, its pharmacological value is limited by its short half-life (approximately 12 min. following intravenous injection in humans), mainly due its susceptibility to rapid enzymatic degradation (Frohman, L. A. et al., *Journal of Clinical Investigation* 1986, 78: 906-913).

There is thus a need for the development of novel GRF analogs exhibiting agonist properties toward the GRF receptor or GHRH receptor (GHRHr).

The present description refers to a number of documents, the content of which is herein incorporated by reference in their entirety.

SUMMARY OF THE INVENTION

The present invention relates to GRF analogs, and uses thereof.

In a first aspect, the present invention provides a growth hormone releasing factor (GRF) analog comprising a domain of formula (I) (SEQ ID NO: 1):

X1-X2-Asp-Ala-Ile-Phe-Thr-X8-X9-Tyr-X11-X12-X13-Leu-X15-Gln-Leu-X18-X19-Arg-Gln-X22-X23-X24-X25-X26-X27-X28-X29-X30-X31-X32-X33 (I)

wherein:

X1 is Tyr or His; X2 is Ala, D-Ala, Ser, Leu, α-aminoisobutyric acid (Aib), Val or Gly; X8 is Asn, Asp, Ala, Gln, Ser or Aib; X9 is Ser, Asp or Ala; X11 is Arg or L-Homoarginine; X12 is Lys, L-Ornithine or L-Homoarginine; X13 is Val or Ile; X15 is Gly or Ala; X18 is Lys, L-Ornithine, L-2,4-diaminobutyric acid, L-2,3-diaminopropionic acid or Ser; X19 is Ala or Leu X22 is Asp or Glu; X23 is Ile or Leu; X24 is Met, Ile, Nle or Leu; X25 is Ser, Asn, Aib or Ala; X26 is Arg, D-Arg, L-Homoarginine or Lys; X27 is Ala or is absent; X28 is Ala or is absent; X29 is Arg or is absent; X30 is Ala or is absent; X31 is Ala or is absent; X32 is Arg or is absent; X33 is HoSer or is absent;

and wherein if X18 is Ser, X27 to X32 or X27 to X33 are present, or a pharmaceutically acceptable salt thereof.

In an embodiment, X1 is Tyr. In an embodiment, X2 is Ala or D-Ala. In an embodiment, X8 is Ala or Asp, in a further embodiment Asp. In an embodiment, X9 is Ser. In an embodiment, X11 is Arg. In an embodiment, X12 is Lys or L-Homoarginine, in a further embodiment Lys. In an embodiment, X15 is Ala. In an embodiment, X18 is L-Ornithine or Lys, in a further embodiment Lys. In an embodiment, X22 is Asp. In an embodiment, X23 is Ile. In an embodiment, X24 is Leu. In an embodiment, X25 is Ala or Ser, in a further embodiment Ala. In an embodiment, X26 is Arg or D-Arg, in a further embodiment Arg. In an embodiment, X27 is Ala. In an embodiment, X28 is Ala. In an embodiment, X29 is Arg. In an embodiment, X30 is Ala. In an embodiment, X31 is Ala. In an embodiment, X32 is Arg. In an embodiment X33 is HoSer.

In another embodiment, at least one of X27 to X33 is/are absent. In a further embodiment, X27 to X33 are absent.

In an embodiment, the above-mentioned domain is: Y-A-D-A-I-F-T-D-S-Y-R-K-V-L-A-Q-L-K-A-R-Q-D-I-L-A-R (SEQ ID NO: 2); Y-a-D-A-I-F-T-D-S-Y-R-K-V-L-A-Q-L-K-A-R-Q-D-I-L-S-r (SEQ ID NO: 3); Y-a-D-A-I-F-T-D-S-Y-R-K-V-L-A-Q-L-K-A-R-Q-D-I-L-aib-R (SEQ ID NO: 4); Y-a-D-A-I-F-T-D-S-Y-R-K-V-L-A-Q-L-O-A-R-Q-D-I-L-S-r (SEQ ID NO: 5); Y-A-D-A-I-F-T-D-S-Y-R-K-V-L-A-Q-L-O-A-R-Q-D-I-L-S-r (SEQ ID NO: 6); Y-a-D-A-I-F-T-D-S-Y-R-K-V-L-A-Q-L-K-A-R-Q-D-L-L-S-r (SEQ ID NO: 7); Y-A-D-A-I-F-T-D-S-Y-R-K-V-L-A-Q-L-K-A-R-Q-D-I-L-A-R-A-A-R (SEQ ID NO: 8); Y-A-D-A-I-F-T-D-S-Y-R-K-V-L-A-Q-L-S-A-R-Q-D-I-L-A-R-A-A-R-A-A-R (SEQ ID NO: 9); Y-a-D-A-I-F-T-D-S-Y-R-K-V-L-A-Q-L-K-A-R-Q-D-I-L-A-R-A-A-R-A-A-R (SEQ ID NO: 10); Y-a-D-A-I-F-

T-D-S-Y-R-K-V-L-A-Q-L-K-L-R-Q-D-I-L-A-R-A-A-R-A-A-R (SEQ ID NO: 11); Y-a-D-A-I-F-T-D-S-Y-R-K-V-L-A-Q-L-K-A-R-Q-D-L-L-A-R-A-A-R-A-A-R (SEQ ID NO: 12); Y-A-D-A-I-F-T-D-S-Y-R-K-V-L-A-Q-L-K-A-R-Q-D-I-L-A-R-A-A-R-A-A-R (SEQ ID NO: 13); Y-A-D-A-I-F-T-D-S-Y-R-K-V-L-A-Q-L-K-A-R-Q-D-L-L-A-R-A-A-R-A-A-R (SEQ ID NO: 14); Y-S-D-A-I-F-T-D-S-Y-R-K-V-L-A-Q-L-K-A-R-Q-D-I-L-A-R-A-A-R-A-A-R (SEQ ID NO: 15); Y-G-D-A-I-F-T-D-S-Y-R-K-V-L-A-Q-L-K-A-R-Q-D-I-L-A-R-A-A-R-A-A-R (SEQ ID NO: 16); Y-L-D-A-I-F-T-D-S-Y-R-K-V-L-A-Q-L-K-A-R-Q-D-I-L-A-R-A-A-R-A-A-R (SEQ ID NO: 17); Y-G-D-A-I-F-T-D-S-Y-R-K-V-L-A-Q-L-K-A-R-Q-D-I-L-A-R-A-A-R-A-A-R-HoSer (SEQ ID NO: 18); Y-a-D-A-I-F-T-D-S-Y-R-K-V-L-A-Q-L-K-A-R-Q-D-I-L-A-R-A-A-R-A-A-R-HoSer (SEQ ID NO: 19);

wherein a=D-Ala, O=L-Ornithine, Aib=α-aminoisobutyric acid, HoSer=L-homoserine and r=D-Arg.

In an embodiment, the above-mentioned GRF analog further comprises (i) an amino-terminal modifying group; (ii) a carboxy-terminal modifying group; or (iii) both (i) and (ii).

In a further embodiment, the above-mentioned amino-terminal modifying group is a linear or branched saturated $C_1$-$C_6$ acyl group or unsaturated $C_3$-$C_6$ acyl group. In yet a further embodiment, the above-mentioned amino-terminal modifying group is an acetyl group (Ac). In another embodiment, the above-mentioned amino-terminal modifying group is a trans-3-hexenoyl group.

In a further embodiment, the above-mentioned carboxy-terminal modifying group is $NH_2$.

In embodiments, the above-mentioned GRF analog is: Trans-3-hexenoyl-Y-A-D-A-I-F-T-D-S-Y-R-K-V-L-A-Q-L-K-A-R-Q-D-I-L-A-R-NH$_2$ (SEQ ID NO: 20); Y-a-D-A-I-F-T-D-S-Y-R-K-V-L-A-Q-L-K-A-R-Q-D-I-L-S-r-NH$_2$ (SEQ ID NO: 21); Y-a-D-A-I-F-T-D-S-Y-R-K-V-L-A-Q-L-K-A-R-Q-D-I-L-aib-R-NH$_2$ (SEQ ID NO: 22); Y-a-D-A-I-F-T-D-S-Y-R-K-V-L-A-Q-L-O-A-R-Q-D-I-L-S-r-NH$_2$ (SEQ ID NO: 23); Trans-3-hexenoyl-Y-A-D-A-I-F-T-D-S-Y-R-K-V-L-A-Q-L-O-A-R-Q-D-I-L-S-r-NH$_2$ (SEQ ID NO: 24); Y-a-D-A-I-F-T-D-S-Y-R-K-V-L-A-Q-L-K-A-R-Q-D-L-L-S-r-NH$_2$ (SEQ ID NO: 25); Trans-3-hexenoyl-Y-A-D-A-I-F-T-D-S-Y-R-K-V-L-A-Q-L-K-A-R-Q-D-I-L-A-R-A-A-R-NH$_2$ (SEQ ID NO: 26); Trans-3-hexenoyl-Y-A-D-A-I-F-T-D-S-Y-R-K-V-L-A-Q-L-S-A-R-Q-D-I-L-A-R-A-A-R-A-A-R-NH$_2$ (SEQ ID NO: 27); Y-a-D-A-I-F-T-D-S-Y-R-K-V-L-A-Q-L-K-A-R-Q-D-I-L-A-R-A-A-R-A-A-R-NH$_2$ (SEQ ID NO: 28); Y-a-D-A-I-F-T-D-S-Y-R-K-V-L-A-Q-L-K-L-R-Q-D-I-L-A-R-A-A-R-A-A-R-NH$_2$ (SEQ ID NO: 29); Y-a-D-A-I-F-T-D-S-Y-R-K-V-L-A-Q-L-K-A-R-Q-D-L-L-A-R-A-A-R-A-A-R-NH$_2$ (SEQ ID NO: 30); Trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31); Trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32); Y-S-D-A-I-F-T-D-S-Y-R-K-V-L-A-Q-L-K-A-R-Q-D-I-L-A-R-A-A-R-A-A-R-NH$_2$ (SEQ ID NO: 33); Y-G-D-A-I-F-T-D-S-Y-R-K-V-L-A-Q-L-K-A-R-Q-D-I-L-A-R-A-A-R-A-A-R-NH$_2$ (SEQ ID NO: 34); Y-L-D-A-I-F-T-D-S-Y-R-K-V-L-A-Q-L-K-A-R-Q-D-I-L-A-R-A-A-R-A-A-R-NH$_2$ (SEQ ID NO: 35); Y-G-D-A-I-F-T-D-S-Y-R-K-V-L-A-Q-L-K-A-R-Q-D-I-L-A-R-A-A-R-A-A-R-HoSer-NH$_2$ (SEQ ID NO: 36); or Y-a-D-A-I-F-T-D-S-Y-R-K-V-L-A-Q-L-K-A-R-Q-D-I-L-A-R-A-A-R-A-A-R-HoSer-NH$_2$ (SEQ ID NO: 37);

wherein a=D-Ala, O=L-Ornithine, Aib=α-aminoisobutyric acid, and r=D-Arg.

In a further embodiment, the above-mentioned GRF analog is Y-a-D-A-I-F-T-D-S-Y-R-K-V-L-A-Q-L-K-A-R-Q-D-I-L-A-R-A-A-R-A-A-R-NH$_2$ (SEQ ID NO: 28).

In another further embodiment, the above-mentioned GRF analog is Y-a-D-A-I-F-T-D-S-Y-R-K-V-L-A-Q-L-K-L-R-Q-D-I-L-A-R-A-A-R-A-A-R-NH$_2$ (SEQ ID NO: 29).

In another further embodiment, the above-mentioned GRF analog is Y-a-D-A-I-F-T-D-S-Y-R-K-V-L-A-Q-L-K-A-R-Q-D-L-L-A-R-A-A-R-A-A-R-NH$_2$ (SEQ ID NO: 30).

In another further embodiment, the above-mentioned GRF analog is trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31).

In another further embodiment, the above-mentioned GRF analog is trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32).

In another aspect, the present invention provides a pharmaceutical composition comprising the above-mentioned GRF analog.

In an embodiment, the above-mentioned pharmaceutical composition further comprises one or more pharmaceutically acceptable carriers, excipients, and/or diluents.

In an aspect, the present invention provides a method for inducing growth hormone secretion in a subject in need thereof, said method comprising administering to said subject an effective amount of the above-mentioned GRF analog or pharmaceutical composition.

In another aspect, the present invention provides a use of the above-mentioned GRF analog or pharmaceutical composition, for inducing growth hormone secretion in a subject.

In another aspect, the present invention provides a use of the above-mentioned GRF analog or pharmaceutical composition, for the preparation of a medicament for inducing growth hormone secretion in a subject.

In another aspect, the present invention provides the above-mentioned GRF analog or pharmaceutical composition, for the preparation of a medicament for inducing growth hormone secretion in a subject.

In another aspect, the present invention provides the above-mentioned GRF analog or pharmaceutical composition, for inducing growth hormone secretion in a subject.

In another aspect, the present invention provides a use of the above-mentioned GRF analog or pharmaceutical composition, as a medicament.

In another aspect, the present invention provides the above-mentioned GRF analog or pharmaceutical composition, for use as a medicament.

In an embodiment, the above-mentioned GRF analog is administered or is adapted for administration at a daily dose of about 0.1 mg to about 20 mg.

In embodiments, the above-mentioned GRF analog is administered, or is adapted for administration, intravenously, orally, transdermally, subcutaneously, mucosally, intramuscularly, intranasally, intrapulmonary, parenterally, intrarectally or topically, in further embodiments subcutaneously or transdermally.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present inventors have discovered novel GRF analogs that exhibit an agonistic activity on cells expressing the GHRHr, and induce GH secretion in animal models.

Native human GRF is a peptide of 44 amino acids having the following structure: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu (SEQ ID NO:38).

The 29 amino acid N-terminal fragment of GRF$_{(1-44)}$, known as GRF$_{(1-29)}$, has been shown to exhibit biological activity and potency that is similar to GRF$_{(1-44)}$. GRF$_{(1-29)}$ has the following sequence: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg (SEQ ID NO:39).

Intermediates forms (in length) between GRF$_{(1-29)}$ and GRF$_{(1-44)}$, i.e., having the sequence of GRF$_{(1-29)}$ at the C-terminus of which 1-14 amino acids are added which correspond to residues 30-43 of native human GRF (or other residues), also possess GRF activity. Further, certain GRF variants having one or more amino acid substitutions in the native sequence are known to possess GRF activity.

The GRF analogs of the present invention are variants of GRF and active fragments and/or variants thereof, comprising a 3 amino acid residue deletion at positions corresponding to residues 21 to 23 (Lys-Leu-Leu underlined in the sequences depicted above) of the native human GRF$_{(1-44)}$, its N-terminal fragment GRF$_{(1-29)}$, or the intermediate forms noted above. The GRF analog of the invention may further comprise an alteration of the serine corresponding to position 18 (in italics in the sequences depicted above), preferably a substitution with Lys, L-Ornithine, L-2,4-diaminobutyric acid or L-2,3-diaminopropionic acid, of the native human GRF$_{(1-44)}$, its N-terminal fragment GRF$_{(1-29)}$, or the intermediate forms noted above. These GRF analogs exhibit agonistic activity on cells expressing the GHRHr, and induce GH secretion in animal models.

The terms "GRF analog", "GRF receptor agonist", "GRF peptide", "GRF peptide compound" or "peptide compound" are used interchangeably herein to refer to the compounds of the present invention that exhibit an agonistic activity on cells expressing the GHRHr and induce GH secretion in animal models, which are described in further detail below. The terms "GRF" (growth hormone-releasing factor) and "GHRH" (growth hormone-releasing hormone) are used interchangeably herein. Similarly, the terms "GRF receptor", "GRFr", "GHRH receptor" and "GHRHr" are used interchangeably herein.

The present invention provides a growth hormone releasing factor (GRF) analog comprising a domain of formula (I) (SEQ ID NO: 1):

X1-X2-Asp-Ala-Ile-Phe-Thr-X8-X9-Tyr-X11-X12-X13-Leu-X15-Gln-Leu-X18-X19-Arg-Gln-X22-X23-X24-X25-X26-X27-X28-X29-X30-X31-X32-X33 (I)

wherein: X1 is Tyr or His; X2 is Ala, D-Ala, Ser, Leu, α-aminoisobutyric acid (Aib), Val or Gly; X8 is Asn, Asp, Ala, Gln, Ser or Aib; X9 is Ser, Asp or Ala; X11 is Arg or L-Homoarginine; X12 is Lys, L-Ornithine or L-Homoarginine; X13 is Val or Ile; X15 is Gly or Ala; X18 is Lys, L-Ornithine, L-2,4-diaminobutyric acid, L-2,3-diaminopropionic acid or Ser; X19 is Ala or Leu X22 is Asp or Glu; X23 is Ile or Leu; X24 is Met, Ile, Nle or Leu; X25 is Ser, Asn, Aib or Ala; X26 is Arg, D-Arg, L-Homoarginine or Lys; X27 is Ala or is absent; X28 is Ala or is absent; X29 is Arg or is absent; X30 is Ala or is absent; X31 is Ala or is absent; X32 is Arg or is absent; X33 is HoSer or is absent;

and wherein if X18 is Ser, X27 to X32 or X27 to X33 are present, or a pharmaceutically acceptable salt thereof.

The present invention further provides a growth hormone releasing factor (GRF) analog comprising a domain of formula (II) (SEQ ID NO: 40):

X1-X2-Asp-Ala-Ile-Phe-Thr-X8-X9-Tyr-X11-X12-X13-Leu-X15-Gln-Leu-X18-X19-Arg-Gln-X22-X23-X24-X25-X26-X27-X28-X29-X30-X31-X32-X33 (II)

wherein: X1 is any amino acid, in an embodiment Tyr or His, in a further embodiment Tyr; X2 is any amino acid, in an embodiment Ala, D-Ala, Ser, Leu, α-aminoisobutyric acid (Aib), Val or Gly, in a further embodiment Ala or D-Ala; X8 is any amino acid, in an embodiment Asn, Asp, Ala, Gln, Ser or Aib, in a further embodiment Ala or Asp, in a further embodiment Asp; X9 is any amino acid, in an embodiment Ser, Asp or Ala, in a further embodiment Ser; X11 is any amino acid, in an embodiment Arg or L-Homoarginine, in a further embodiment Arg; X12 is any amino acid, in an embodiment Lys, L-Ornithine or L-homoarginine, in a further embodiment Lys or L-homoarginine, in yet a further embodiment Lys; X13 is any amino acid, in an embodiment Val or Ala, in a further embodiment Val; X15 is any amino acid, in an embodiment Gly or Ala, in a further embodiment Ala; X18 is any amino acid, in an embodiment Lys, L-Ornithine, L-2,4-diaminobutyric acid or L-2,3-diaminopropionic acid, in a further embodiment Lys or L-Ornithine, in yet a further embodiment Lys; X19 is Ala or Leu; X22 is any amino acid, in an embodiment Asp or Glu, in a further embodiment Asp; X23 is any amino acid, in an embodiment Ile or Leu, in a further embodiment Ile; X24 is any amino acid, in an embodiment Met, Ile, Nle or Leu, in a further embodiment Met or Leu, in a further embodiment Leu; X25 is any amino acid, in an embodiment Ser, Asn, Aib or Ala, in a further embodiment Ala or Ser, in yet a further embodiment Ala; X26 is any amino acid, in an embodiment Arg, D-Arg, L-Homoarginine or Lys, in a further embodiment Arg or D-Arg, in yet a further embodiment Arg; X27 is any amino acid, in an embodiment Ala, or is absent; X28 is any amino acid, in an embodiment Ala, or is absent; X29 is any amino acid, in an embodiment Arg, or is absent; X30 is any amino acid, in an embodiment Ala, or is absent; X31 is any amino acid, in an embodiment Ala or is absent; X32 is any amino acid, in an embodiment Arg, or is absent; and X33 is any amino acid, in an embodiment HoSer, or is absent;

and wherein if X18 is Ser, X27 to X32 or X27 to X33 are present, or a pharmaceutically acceptable salt thereof.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc.

Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Hoarg), N-acetyl lysine, 2-amino butyric acid, 2-amino butyric acid, 2,4-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry.

In embodiments, domains or GRF analogs of the present invention include polypeptides with altered sequences containing substitutions of functionally equivalent amino acid residues, relative to the above-mentioned domains or GRF analogs. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

The above-mentioned domain or GRF analog may comprise all L-amino acids, all D-amino acids or a mixture of L- and D-amino acids. In an embodiment, the above-mentioned domain or GRF analog comprises at least one D-amino acid (e.g., 1, 2, 3, 4, 5 or more D-amino acids). In an embodiment, the above-mentioned domain or GRF analog comprises at least one D-Ala and/or D-Arg residue. In an embodiment, said at least one D-amino acid is located in the N-terminal and/or C-terminal portion of the domain or GRF analog (e.g., within the last 2 or 3 N- and/or C-terminal residues). The presence of one or more D-amino acids typically results in peptides having increased stability (e.g., in vivo) due to decreased susceptibility to protease/peptidase cleavage, but which retain biological activity.

In embodiments, the above-mentioned GRF analog is in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or may be prepared separately by reacting a free base function with a suitable acid. Many of the GRF analogs disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, decanoate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, octanoate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

In an embodiment, in formula (I) and/or (II), X30 to X32 are absent. In another embodiment, X30 to X33 are absent.

In another embodiment, in formula (I) and/or (II), X27 to X29 are as follows: Ala-Ala-Arg.

In another embodiment, in formula (I) and/or (II), X27 to X32 are absent. In another embodiment, X27 to X33 are absent.

In another embodiment, in formula (I) and/or (II), X18 is Lys and X27 to X29, X27 to X32 or X27 to X33 are present. In an embodiment, X27 to X32 are as follows: Ala-Ala-Arg-Ala-Ala-Arg (SEQ ID NO: 41). In an embodiment, X27 to X33 are as follows: Ala-Ala-Arg-Ala-Ala-Arg-HoSer (SEQ ID NO: 42).

In an embodiment, the above-mentioned GRF analog comprises one domain of formula I or II as defined above. In an embodiment, the above-mentioned GRF analog comprises two or more (e.g., 2, 3, 4 or 5) domains of formula I or II as defined above.

In embodiments, the above-mentioned GRF analog may comprise, further to the domain of formula I or II defined above, one more amino acids (naturally occurring or synthetic) covalently linked to the amino- and/or carboxy-termini of said domain. In an embodiment, the above-mentioned GRF analog comprises up to 25 additional amino acids at the N- and/or C-termini to the domain of formula (I) or (II) defined above. In further embodiments, the above-mentioned GRF analog comprises up to 20, 19, 18, 17, 16, 15, 14, 13, 12, 11, 10, 9, 8, 7, 6, 5, 4, 3, 2, or 1 additional amino acids at the N- and/or C-termini of the domain of formula (I) or (II) defined above. In an embodiment, the above-mentioned domain or GRF analog contains about 100 residues or less, in further embodiments about 90, 80, 70, 60, 50, 40 or 35 residues or less. In an embodiment, the above-mentioned domain or GRF analog contains between about 26 residues to about 100 residues. In a further embodiment, the above-mentioned domain or GRF analog contains between about 26 residues to about 50 residues. In a further embodiment, the above-mentioned GRF analog contains between about 26 residues to about 45 residues. In a further embodiment, the above-mentioned GRF analog contains between about 26 residues to about 40 residues. In a further embodiment, the above-mentioned GRF analog contains about 26, 27, 28, 29, 30, 31, 32, 33, 34, 35, 36, 37, 38 or 39 residues.

In an embodiment, the above-mentioned domain or GRF analog is a peptidomimetic. A peptidomimetic is typically characterised by retaining the polarity, three dimensional size and functionality (bioactivity) of its peptide equivalent, but wherein one or more of the peptide bonds/linkages have been replaced, often by more stable linkages. Generally, the bond which replaces the amide bond (amide bond surrogate) conserves many or all of the properties of the amide bond, e.g. conformation, steric bulk, electrostatic character, potential for hydrogen bonding, etc. Typical peptide bond replacements include esters, polyamines and derivatives thereof as well as substituted alkanes and alkenes, such as aminomethyl and ketomethylene. For example, the above-mentioned domain or GRF analog may have one or more peptide linkages replaced by linkages such as —CH$_2$NH—, —CH$_2$S—, —CH$_2$—CH$_2$—, —CH═CH— (cis or trans), —CH$_2$SO—, —CH(OH)CH$_2$—, or —COCH$_2$—. Such peptidomimetics may have greater chemical stability, enhanced biological/pharmacological properties (e.g., half-life, absorption, potency, efficiency, etc.) and/or reduced antigenicity relative its peptide equivalent.

In embodiments, the GRF analog consists of the domain of formula (I) or (II) defined above.

In embodiments, the above-mentioned domain comprises one of the following sequences: Y-A-D-A-I-F-T-D-S-Y-R-K-V-L-A-Q-L-K-A-R-Q-D-I-L-A-R (SEQ ID NO: 2); Y-a-D-A-I-F-T-D-S-Y-R-K-V-L-A-Q-L-K-A-R-Q-D-I-L-S-r (SEQ ID NO: 3); Y-a-D-A-I-F-T-D-S-Y-R-K-V-L-A-Q-L-K-A-R-Q-D-I-L-aib-R (SEQ ID NO: 4); Y-a-D-A-I-F-T-D-S-Y-R-K-V-L-A-Q-L-O-A-R-Q-D-I-L-S-r (SEQ ID NO: 5); Y-A-D-A-I-F-T-D-S-Y-R-K-V-L-A-Q-L-O-A-R-Q-D-I-L-S-r (SEQ ID NO: 6); Y-a-D-A-I-F-T-D-S-Y-R-K-V-L-A-Q-L-K-A-R-Q-D-L-L-S-r (SEQ ID NO: 7); Y-A-D-A-I-F-T-D-S-Y-R-K-V-L-A-Q-L-K-A-R-Q-D-I-L-A-R-A-A-R (SEQ ID NO: 8); Y-A-D-A-I-F-T-D-S-Y-R-K-V-L-A-Q-L-S-A-R-Q-D-I-L-A-R-A-A-R (SEQ ID NO: 9); Y-a-D-A-I-F-T-D-S-Y-R-K-V-L-A-Q-L-K-A-R-Q-D-I-L-A-R-A-A-R-A-A-R (SEQ ID NO: 10); Y-a-D-A-I-F-T-D-S-Y-R-K-V-L-A-Q-L-K-L-R-Q-D-I-L-A-R-A-A-R-A-A-R (SEQ ID NO: 11); Y-a-D-A-I-F-T-D-S-Y-R-K-V-L-A-Q-L-K-A-R-Q-D-L-L-A-R-A-A-R-A-A-R (SEQ ID NO: 12); Y-A-D-A-I-F-T-D-S-Y-R-K-V-L-A-Q-L-K-A-R-Q-D-I-L-A-R-A-A-R-A-A-R (SEQ ID NO: 13); Y-A-D-A-I-F-T-D-S-Y-R-K-V-L-A-Q-L-K-A-R-Q-D-L-L-A-R-A-A-R-A-A-R (SEQ ID NO: 14); Y-S-D-A-I-F-T-D-S-Y-R-K-V-L-A-Q-L-K-A-R-Q-D-I-L-A-R-A-A-R-A-A-R (SEQ ID NO: 15); Y-G-D-A-I-F-T-D-S-Y-R-K-V-L-A-Q-L-K-A-R-Q-D-I-L-A-R-A-A-R-A-A-R (SEQ ID NO: 16); Y-L-D-A-I-F-T-D-S-Y-R-K-V-L-A-Q-L-K-A-R-Q-D-I-L-A-R-A-A-R-A-A-R (SEQ ID NO: 17); Y-G-D-A-I-F-T-D-S-Y-R-K-V-L-A-Q-L-K-A-R-Q-D-I-L-A-R-A-A-R-A-A-R-HoSer (SEQ ID NO: 18); Y-a-D-A-I-F-T-D-S-Y-R-K-V-L-A-Q-L-K-A-R-Q-D-I-L-A-R-A-A-R-A-A-R-HoSer (SEQ ID NO: 19);

wherein a=D-Ala, O=L-Ornithine, Aib=α-aminoisobutyric acid, HoSer=L-homoserine and r=D-Arg.

In further embodiments, the above-mentioned domain comprises one of the following sequences: Y-A-D-A-I-F-T-D-S-Y-R-K-V-L-A-Q-L-K-A-R-Q-D-I-L-A-R-A-A-R (SEQ ID NO: 8); Y-A-D-A-I-F-T-D-S-Y-R-K-V-L-A-Q-L-S-A-R-Q-D-I-L-A-R-A-A-R (SEQ ID NO: 9); Y-a-D-A-1-F-T-D-S-Y-R-K-V-L-A-Q-L-K-A-R-Q-D-I-L-A-R-A-A-R-A-A-R (SEQ ID NO: 10); Y-a-D-A-I-F-T-D-S-Y-R-K-V-L-A-Q-L-K-L-R-Q-D-I-L-A-R-A-A-R-A-A-R (SEQ ID NO: 11); Y-a-D-A-I-F-T-D-S-Y-R-K-V-L-A-Q-L-K-A-R-Q-D-L-L-A-R-A-A-R-A-A-R (SEQ ID NO: 12); Y-A-D-A-I-F-T-D-S-Y-R-K-V-L-A-Q-L-K-A-R-Q-D-I-L-A-R-A-A-R-A-A-R (SEQ ID NO: 13); or Y-A-D-A-I-F-T-D-S-Y-R-K-V-L-A-Q-L-K-A-R-Q-D-L-L-A-R-A-A-R-A-A-R (SEQ ID NO: 14), wherein a=D-Ala.

In embodiments, the above-mentioned domain is (or consists of): Y-A-D-A-I-F-T-D-S-Y-R-K-V-L-A-Q-L-K-A-R-Q-D-I-L-A-R (SEQ ID NO: 2); Y-a-D-A-I-F-T-D-S-Y-R-K-V-L-A-Q-L-K-A-R-Q-D-I-L-S-r (SEQ ID NO: 3); Y-a-D-A-I-F-T-D-S-Y-R-K-V-L-A-Q-L-K-A-R-Q-D-I-L-aib-R (SEQ ID NO: 4); Y-a-D-A-I-F-T-D-S-Y-R-K-V-L-A-Q-L-O-A-R-Q-D-I-L-S-r (SEQ ID NO: 5); Y-A-D-A-I-F-T-D-S-Y-R-K-V-L-A-Q-L-O-A-R-Q-D-I-L-S-r (SEQ ID NO: 6); Y-a-D-A-I-F-T-D-S-Y-R-K-V-L-A-Q-L-K-A-R-Q-D-L-L-S-r (SEQ ID NO: 7); Y-A-D-A-I-F-T-D-S-Y-R-K-V-L-A-Q-L-K-A-R-Q-D-I-L-A-R-A-A-R (SEQ ID NO: 8); Y-A-D-A-I-F-T-D-S-Y-R-K-V-L-A-Q-L-S-A-R-Q-D-I-L-A-R-A-A-R (SEQ ID NO: 9); Y-a-D-A-I-F-T-D-S-Y-R-K-V-L-A-Q-L-K-A-R-Q-D-I-L-A-R-A-A-R-A-A-R (SEQ ID NO: 10); Y-a-D-A-I-F-T-D-S-Y-R-K-V-L-A-Q-L-K-L-R-Q-D-I-L-A-R-A-A-R-A-A-R (SEQ ID NO: 11); Y-a-D-A-I-F-T-D-S-Y-R-K-V-L-A-Q-L-K-A-R-Q-D-L-L-A-R-A-A-R-A-A-R (SEQ ID NO: 12); Y-A-D-A-I-F-T-D-S-Y-R-K-V-L-A-Q-L-K-A-R-Q-D-I-L-A-R-A-A-R-A-A-R (SEQ ID NO: 13); or Y-A-D-A-I-F-T-D-S-Y-R-K-V-L-A-Q-L-K-A-R-Q-D-L-L-A-R-A-A-R-A-A-R (SEQ ID NO: 14), wherein a=D-Ala.

In a further embodiment, the above-mentioned domain is Y-A-D-A-I-F-T-D-S-Y-R-K-V-L-A-Q-L-K-A-R-Q-D-I-L-A-R-A-A-R (SEQ ID NO: 8).

In a further embodiment, the above-mentioned domain is Y-A-D-A-I-F-T-D-S-Y-R-K-V-L-A-Q-L-S-A-R-Q-D-I-L-A-R-A-A-R (SEQ ID NO: 9).

In a further embodiment, the above-mentioned domain is Y-a-D-A-I-F-T-D-S-Y-R-K-V-L-A-Q-L-K-A-R-Q-D-I-L-A-R-A-A-R-A-A-R (SEQ ID NO: 10), wherein a=D-Ala.

In a further embodiment, the above-mentioned domain is Y-a-D-A-I-F-T-D-S-Y-R-K-V-L-A-Q-L-K-L-R-Q-D-I-L-A-R-A-A-R-A-A-R (SEQ ID NO: 11), wherein a=D-Ala.

In a further embodiment, the above-mentioned domain is Y-a-D-A-I-F-T-D-S-Y-R-K-V-L-A-Q-L-K-A-R-Q-D-L-L-A-R-A-A-R-A-A-R (SEQ ID NO: 12), wherein a=D-Ala.

In a further embodiment, the above-mentioned domain is Y-A-D-A-I-F-T-D-S-Y-R-K-V-L-A-Q-L-K-A-R-Q-D-I-L-A-R-A-A-R-A-A-R (SEQ ID NO: 13).

In a further embodiment, the above-mentioned domain is Y-A-D-A-I-F-T-D-S-Y-R-K-V-L-A-Q-L-K-A-R-Q-D-L-L-A-R-A-A-R-A-A-R (SEQ ID NO: 14).

In embodiments, the N- and/or C-terminal amino acids of the above-mentioned GRF analog or domain may be modified, for example by amidation, acetylation, acylation or any other modifications known in the art.

Accordingly, in another aspect, the present invention provides a GRF analog of formula (III):

Z1-X1-X2-Asp-Ala-Ile-Phe-Thr-X8-X9-Tyr-X11-X12-X13-Leu-X15-Gln-Leu-X18-X19-Arg-Gln-X22-X23-X24-X25-X26-X27-X28-X29-X30-X31-X32-X33-Z2 (III)

or

Z1-[domain of formula I or II]-Z2

Wherein X1, X2, X8, X9, X11 to X13, X15, X18, X19 and X22 to X33 are as defined above; Z1 is an amino-terminal modification or is absent; and Z2 is a carboxy-terminal modification or is absent.

In an embodiment, the amino terminal residue (i.e., the free amino group at the N-terminal end) of the GRF analog is modified (e.g., for protection against degradation), for example by covalent attachment of a moiety/chemical group (Z1). In an embodiment, the amino-terminal modification (Z1) is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), in a further embodiment an acetyl group ($CH_3$—CO—, Ac). In another embodiment, Z1 is a sequence of one or more amino acids (e.g., 1 to 25 additional amino acids, for example 20, 19, 18, 17, 16, 15, 14, 13, 12, 11, 10, 9, 8, 7, 6, 5, 4, 3, 2, or 1 amino acids) attached to X1. In an embodiment, if Z1 is absent, X2 is D-Ala.

In another embodiment, the amino-terminal modification (Z1) is a hydrophobic tail comprising a backbone of 5 to 8 atoms; wherein the backbone can be substituted by $C_{1-6}$ alkyl, $C_{3-6}$ cycloalkyl, or $C_{6-12}$ aryl $C_{1-6}$ alkyl, $C_{3-6}$ cycloalkyl, or $C_{6-12}$ aryl and the backbone comprises at least one rigidifying moiety connected to at least two atoms of the backbone; and the rigidifying moiety is a double bond, a triple bond, a saturated or unsaturated $C_{3-9}$ cycloalkyl, or a $C_{6-12}$ aryl. In a further embodiment, Z1 is (i)

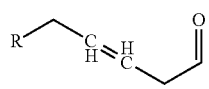

wherein R is H, $CH_3$ or $CH_2CH_3$, and the double bond is cis or trans;

(ii)

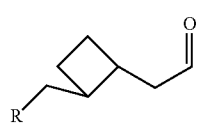

wherein R is H, $CH_3$ or $CH_2CH_3$, wherein X is in a cis or trans configuration, and wherein said GRF analog is a racemic mixture or a pure enantiomer;

(iii)

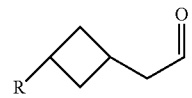

wherein R is H, $CH_3$ or $CH_2CH_3$, and wherein when R is $CH_3$ or $CH_2CH_3$, X is in a cis or trans configuration;

(iv)

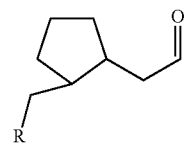

wherein R is H, $CH_3$ or $CH_2CH_3$, wherein X is in a cis or trans configuration, and wherein said GRF analog is a racemic mixture or a pure enantiomer;

(v)

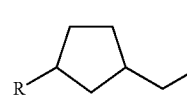

wherein R is H, $CH_3$ or $CH_2CH_3$, wherein when R is $CH_3$ or $CH_2CH_3$, X is in a cis or trans configuration, and wherein said GRF analog is a racemic mixture or a pure enantiomer;

(vi)

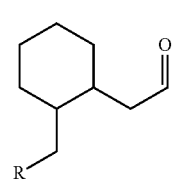

wherein R is H, $CH_3$ or $CH_2CH_3$, wherein X is in a cis or trans configuration, and wherein said GRF analog is a racemic mixture or a pure enantiomer;

(vii)

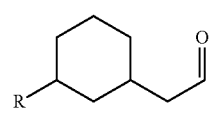

wherein R is H, $CH_3$ or $CH_2CH_3$, wherein when R is $CH_3$ or $CH_2CH_3$, X is in a cis or trans configuration, and wherein said GRF analog is a racemic mixture or a pure enantiomer;

(viii)

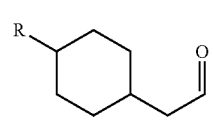

wherein R is H, $CH_3$ or $CH_2CH_3$, and wherein when R is $CH_3$ or $CH_2CH_3$, X is in a cis or trans configuration;

(ix)

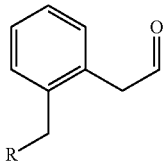

wherein R is H, CH₃ or CH₂CH₃;

(x)

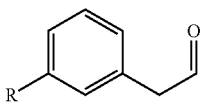

wherein R is H, CH₃ or CH₂CH₃;

(xi)

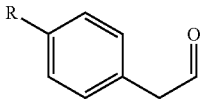

wherein R is H, CH₃ or CH₂CH₃; or (xii)

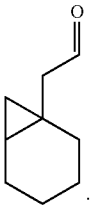

In an embodiment, the amino-terminal modification (Z1) is trans-CH₃—CH₂-CH═CH—CH₂—CO or trans-3-hexenoyl.

In an embodiment, the carboxy terminal residue (i.e., the free carboxy group at the C-terminal end of the peptide) of the GRF analog is modified (e.g., for protection against degradation). In an embodiment, the modification is an amidation (replacement of the OH group by a NH₂ group), thus in such a case Z2 is a NH₂ group. In a further embodiment, Z2 is a sequence of one or more amino acids (e.g., 1 to 25 additional amino acids, for example 20, 19, 18, 17, 16, 15, 14, 13, 12, 11, 10, 9, 8, 7, 6, 5, 4, 3, 2, or 1 amino acids).

The GRF analogs of the present invention may further comprise modifications that confer additional biological properties to the GRF analogs such as protease resistance, plasma protein binding, increased plasma half-life, intracellular penetration, etc. Such modifications include, for example, covalent attachment of fatty acids (e.g., C₆-C₁₈) to the GRF analogs, attachment to proteins such as albumin (see, e.g., U.S. Pat. No. 7,268,113); glycosylation, biotinylation or PEGylation (see, e.g., U.S. Pat. Nos. 7,256,258 and 6,528,485). The above description of modification of the GRF analogs does not limit the scope of the approaches nor the possible modifications that can be engineered.

In embodiments, the above-mentioned GRF analog is: Trans-3-hexenoyl-Y-A-D-A-1-F-T-D-S-Y-R-K-V-L-A-Q-L-K-A-R-Q-D-I-L-A-R-NH₂ (SEQ ID NO: 20); Y-a-D-A-I-F-T-D-S-Y-R-K-V-L-A-Q-L-K-A-R-Q-D-I-L-S-r-NH₂ (SEQ ID NO: 21); Y-a-D-A-I-F-T-D-S-Y-R-K-V-L-A-Q-L-K-A-R-Q-D-I-L-aib-R-NH₂ (SEQ ID NO: 22); Y-a-D-A-I-F-T-D-S-Y-R-K-V-L-A-Q-L-O-A-R-Q-D-I-L-S-r-NH₂ (SEQ ID NO: 23); Trans-3-hexenoyl-Y-A-D-A-I-F-T-D-S-Y-R-K-V-L-A-Q-L-O-A-R-Q-D-I-L-S-r-NH₂ (SEQ ID NO: 24); Y-a-D-A-I-F-T-D-S-Y-R-K-V-L-A-Q-L-K-A-R-Q-D-L-L-S-r-NH₂ (SEQ ID NO: 25); Trans-3-hexenoyl-Y-A-D-A-I-F-T-D-S-Y-R-K-V-L-A-Q-L-K-A-R-Q-D-I-L-A-R-A-A-R-NH₂ (SEQ ID NO: 26); Trans-3-hexenoyl-Y-A-D-A-I-F-T-D-S-Y-R-K-V-L-A-Q-L-S-A-R-Q-D-I-L-A-R-A-A-R-A-A-R-NH₂ (SEQ ID NO: 27); Y-a-D-A-I-F-T-D-S-Y-R-K-V-L-A-Q-L-K-A-R-Q-D-I-L-A-R-A-A-R-A-A-R-NH₂ (SEQ ID NO: 28); Y-a-D-A-I-F-T-D-S-Y-R-K-V-L-A-Q-L-K-L-R-Q-D-I-L-A-R-A-A-R-A-A-R-NH₂ (SEQ ID NO: 29); Y-a-D-A-I-F-T-D-S-Y-R-K-V-L-A-Q-L-K-A-R-Q-D-L-L-A-R-A-A-R-A-A-R-NH₂ (SEQ ID NO: 30); Trans-3-hexenoyl-Y-A-D-A-I-F-T-D-S-Y-R-K-V-L-A-Q-L-K-A-R-Q-D-1-L-A-R-A-A-R-A-A-R-NH₂ (SEQ ID NO: 31); Trans-3-hexenoyl-Y-A-D-A-I-F-T-D-S-Y-R-K-V-L-A-Q-L-K-A-R-Q-D-L-L-A-R-A-A-R-A-A-R-NH₂ (SEQ ID NO: 32); Y-S-D-A-I-F-T-D-S-Y-R-K-V-L-A-Q-L-K-A-R-Q-D-I-L-A-R-A-A-R-A-A-R-NH₂ (SEQ ID NO: 33); Y-G-D-A-I-F-T-D-S-Y-R-K-V-L-A-Q-L-K-A-R-Q-D-I-L-A-R-A-A-R-A-A-R-NH₂ (SEQ ID NO: 34); Y-L-D-A-I-F-T-D-S-Y-R-K-V-L-A-Q-L-K-A-R-Q-D-I-L-A-R-A-A-R-A-A-R-NH₂ (SEQ ID NO: 35); Y-G-D-A-I-F-T-D-S-Y-R-K-V-L-A-Q-L-K-A-R-Q-D-I-L-A-R-A-A-R-A-A-R-HoSer-NH₂ (SEQ ID NO: 36); or Y-a-D-A-I-F-T-D-S-Y-R-K-V-L-A-Q-L-K-A-R-Q-D-I-L-A-R-A-A-R-A-A-R-HoSer-NH₂ (SEQ ID NO: 37); wherein a=D-Ala, O=L-Ornithine, Aib=α-aminoisobutyric acid, r=D-Arg, and HoSer=L-homoserine.

In embodiments, the above-mentioned GRF analog is: Trans-3-hexenoyl-Y-A-D-A-1-F-T-D-S-Y-R-K-V-L-A-Q-L-K-A-R-Q-D-I-L-A-R-A-A-R-NH₂ (SEQ ID NO: 26); Trans-3-hexenoyl-Y-A-D-A-I-F-T-D-S-Y-R-K-V-L-A-Q-L-S-A-R-Q-D-I-L-A-R-A-A-R-A-A-R-NH₂ (SEQ ID NO: 27); Y-a-D-A-I-F-T-D-S-Y-R-K-V-L-A-Q-L-K-A-R-Q-D-I-L-A-R-A-A-R-A-A-R-NH₂ (SEQ ID NO: 28); Y-a-D-A-I-F-T-D-S-Y-R-K-V-L-A-Q-L-K-L-R-Q-D-I-L-A-R-A-A-R-A-A-R-NH₂ (SEQ ID NO: 29); Y-a-D-A-I-F-T-D-S-Y-R-K-V-L-A-Q-L-K-A-R-Q-D-L-L-A-R-A-A-R-A-A-R-NH₂ (SEQ ID NO: 30); Trans-3-hexenoyl-Y-A-D-A-I-F-T-D-S-Y-R-K-V-L-A-Q-L-K-A-R-Q-D-I-L-A-R-A-A-R-A-A-R-NH₂ (SEQ ID NO: 31); Trans-3-hexenoyl-Y-A-D-A-I-F-T-D-S-Y-R-K-V-L-A-Q-L-K-A-R-Q-D-L-L-A-R-A-A-R-A-A-R-NH₂ (SEQ ID NO: 32), wherein a=D-Ala.

In a further embodiment, the above-mentioned GRF analog is trans-3-hexenoyl-Y-A-D-A-I-F-T-D-S-Y-R-K-V-L-A-Q-L-K-A-R-Q-D-I-L-A-R-A-A-R-NH₂ (SEQ ID NO: 26).

In a further embodiment, the above-mentioned GRF analog is trans-3-hexenoyl-Y-A-D-A-I-F-T-D-S-Y-R-K-V-L-A-Q-L-S-A-R-Q-D-I-L-A-R-A-A-R-A-A-R-NH₂ (SEQ ID NO: 27).

In a further embodiment, the above-mentioned GRF analog is Y-a-D-A-I-F-T-D-S-Y-R-K-V-L-A-Q-L-K-A-R-Q-D-I-L-A-R-A-A-R-A-A-R-NH₂ (SEQ ID NO: 28).

In a further embodiment, the above-mentioned GRF analog is Y-a-D-A-I-F-T-D-S-Y-R-K-V-L-A-Q-L-K-L-R-Q-D-I-L-A-R-A-A-R-A-A-R-NH₂ (SEQ ID NO: 29).

In a further embodiment, the above-mentioned GRF analog is Y-a-D-A-I-F-T-D-S-Y-R-K-V-L-A-Q-L-K-A-R-Q-D-L-L-A-R-A-A-R-A-A-R-NH₂ (SEQ ID NO: 30).

In a further embodiment, the above-mentioned GRF analog is trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31).

In a further embodiment, the above-mentioned GRF analog is trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32).

In an embodiment, the above-mentioned GRF analog exhibits a biological activity and/or potency that is similar to, or significantly higher than, a GRF peptide comprising a native sequence (e.g., human GRF$_{(1-44)}$, GRF$_{(1-29)}$, intermediate forms such as GRF$_{(1-40)}$, as well as N-terminal acylated and C-terminally amidated forms thereof). In a further embodiment, the above-mentioned biological activity and/or potency is an in vivo biological activity and/or potency (e.g., in vivo GH secretion activity and/or potency). In a further embodiment, the above-mentioned GRF analog exhibits a biological activity and/or potency that is significantly higher than (or significantly increased relative to) a GRF peptide comprising a native sequence (e.g., GRF$_{(1-29)}$). Such biological activity and/or potency may be measured in animal models, for example the mice and rat models described herein. Significantly higher as used refers to a potency which is at least two-, three, four or five-fold higher than that of a GRF peptide comprising a native sequence (e.g., GRF$_{(1-44)}$, GRF$_{(1-29)}$). In another embodiment, the above-mentioned GRF analog exhibits a stability (e.g., in vivo stability) that is similar to, or significantly higher than, a GRF peptide comprising a native sequence (e.g., human GRF$_{(1-44)}$, GRF$_{(1-29)}$, intermediate forms such as GRF$_{(1-40)}$, as well as N-terminal acylated and C-terminally amidated forms thereof). In a further embodiment, the above-mentioned GRF analog exhibits an in vivo stability (half-life) that is significantly higher than (or significantly increased relative to) a GRF peptide comprising a native GFR sequence (e.g., GRF$_{(1-29)}$).

The GRF analogs of the invention may be produced by expression in a host cell comprising a nucleic acid encoding the GRF analog (recombinant expression) or by chemical synthesis (e.g., solid-phase peptide synthesis). Peptides can be readily synthesized by manual and automated solid phase procedures well known in the art. Suitable syntheses can be performed for example by utilizing "T-boc" or "Fmoc" procedures. Techniques and procedures for solid phase peptide synthesis are described in for example *Solid Phase Peptide Synthesis: A Practical Approach*, by E. Atherton and R. C. Sheppard, published by IRL, Oxford University Press, 1989. Alternatively, the peptides may be prepared by way of segment condensation, as described, for example, in Liu et al., *Tetrahedron Lett*. 37: 933-936, 1996; Baca et al., *J. Am. Chem. Soc*. 117: 1881-1887, 1995; Tam et al., *Int. J. Peptide Protein Res*. 45: 209-216, 1995; Schnolzer and Kent, *Science* 256: 221-225, 1992; Liu and Tam, *J. Am. Chem. Soc*. 116: 4149-4153, 1994; Liu and Tam, *Proc. Natl. Acad. Sci. USA* 91: 6584-6588, 1994; and Yamashiro and Li, *Int. J. Peptide Protein Res*. 31: 322-334, 1988). Other methods useful for synthesizing the peptides are described in Nakagawa et al., *J. Am. Chem. Soc*. 107: 7087-7092, 1985.

Peptides and peptide analogs comprising naturally occurring amino acids encoded by the genetic code may also be prepared using recombinant DNA technology using standard methods. Peptides produced by recombinant technology may be modified (e.g., N-terminal acylation [e.g., acetylation], C-terminal amidation), using methods well known in the art. Therefore, in embodiments, in cases where a GRF analog described herein contains naturally occurring amino acids encoded by the genetic code, the GRF analog may be produced using recombinant methods, and may in embodiments be subjected to for example the just-noted modifications (e.g., acylation, amidation). Accordingly, in another aspect, the invention further provides a nucleic acid encoding the above-mentioned domain or GRF analog. The invention also provides a vector comprising the above-mentioned nucleic acid. In yet another aspect, the present invention provides a cell (e.g., a host cell) comprising the above-mentioned nucleic acid and/or vector. The invention further provides a recombinant expression system, vectors and host cells, such as those described above, for the expression/production of a peptide or GRF analog of the invention, using for example culture media, production, isolation and purification methods well known in the art.

The GRF analogs of the invention can be purified by many techniques of peptide purification well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide or peptide analog may for example be used.

In an embodiment, the above-mentioned GRF analog is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

In another aspect, the present invention provides a composition (e.g., a pharmaceutical composition) comprising the above-mentioned GRF analog. In an embodiment, the composition further comprises one or more pharmaceutically acceptable carriers, excipient, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The term "pharmaceutically acceptable carriers, excipient, and/or diluents" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like (see, e.g., Rowe et al., *Handbook of Pharmaceutical Excipients*, Pharmaceutical Press; 6$^{th}$ edition, 2009).

The GRF analog of the present invention may be formulated for administration via any conventional route, such as intravenous, oral, transdermal, intraperitoneal, subcutaneous, mucosal, intramuscular, intranasal, intrapulmonary, parenteral or topical administration. The preparation of such formulations is well known in the art (see, e.g., *Remington: The Science and Practice of Pharmacy*, Lippincott Williams & Wilkins; 21$^{st}$ edition, 2005).

The GRF analogs and compositions of the invention may be useful for inducing or stimulating the secretion of GH in a subject.

Accordingly, in another aspect, the present invention provides a method for inducing or increasing growth hormone secretion in a subject in need thereof, said method comprising administering to said subject an effective amount of the above-mentioned GRF analog or the above-mentioned pharmaceutical composition.

In another aspect, the present invention provides a use of the above-mentioned GRF analog or the above-mentioned pharmaceutical composition, for inducing or increasing growth hormone secretion in a subject.

In another aspect, the present invention provides a use of the above-mentioned GRF analog or the above-mentioned pharmaceutical composition, for the preparation of a medicament for inducing or increasing growth hormone secretion in a subject.

In another aspect, the present invention provides the above-mentioned GRF analog of or the above-mentioned pharmaceutical composition, for the preparation of a medicament for inducing or increasing growth hormone secretion in a subject.

In another aspect, the present invention provides the above-mentioned GRF analog of or the above-mentioned pharmaceutical composition, for use in inducing or increasing growth hormone secretion in a subject.

The terms "stimulating," "increasing," or "inducing" or any variations of these terms as used herein, refer to a measurable increase of a biological activity. In embodiments, the increase is at least a 10%, 20%, 40%, 60%, 80%, 90%, 95%, 100% (2-fold), 200% (3-fold) increase in the biological activity relative to a control. For example, a GRF analog is found to stimulate GHRHr activity when an increase in GH levels is measured following administration of the GRF analog to a subject (e.g., animal, human) in comparison to a subject not administered with the GRF analog.

In view of their GHRHr agonist activity and GH-releasing properties, the GRF analogs and compositions of the invention may be useful as a medicament, for prophylactic and/or therapeutic applications in which stimulation of GH/IGF-1 secretion is desirable, for example for the treatment or prevention of conditions/disorders/diseases associated with GRF and/or GH function (e.g., in which reduced GH and/or GHRH function is involved in the etiology of the disease/disorder). Diseases and conditions in which administration of GH, GRF or GRF analogs/derivatives may be beneficial have been extensively described in the art (see, e.g., WO 2009/009727, WO 2006/042408, WO 2005/037307, WO 2004/105789). Such conditions/disorders/diseases include, for example, syndromes associated with fat accumulation, hypercholesterolemia, obesity, syndrome X, lipohypertrophy, lipoatrophy, lipodystrophy (e.g., HIV-associated lipodystrophy syndrome), impaired cognitive function, impaired daytime vigilance, declined function of the immune system (e.g., immunodeficiencies such as T-cell deficiencies), muscle protein catabolism, diseases/conditions associated with muscle wasting such as sarcopenia, frailty, radiotherapy- and/or chemotherapy-related side effects (e.g., in HIV-infected and cancer patients), cachexia (e.g., in cancer patients), hypothalamic pituitary dwarfism, burns, osteoporosis, renal failure, non-union bone fracture, acute/chronic debilitating illness or infection, wound healing, post-surgical problems, lactation failure, infertility in women, neurodegenerative conditions, GRF receptor-dependent tumors, conditions related to aging, sleep disorders/impairment.

Therefore, in other aspects, the present invention provides a method for (1) stimulating daytime vigilance and/or cognitive function, e.g. in conditions related to aging, mild cognitive impairment (MCI), pre-Alzheimer's symptoms (Pre-Onset Alzheimer's), dementia and/or sleep impairment (e.g., age-related sleep impairment), (2) improving/preventing/treating metabolic conditions associated with fat accumulation and/or hypercholesterolemia (obesity, abdominal obesity/adiposity, abdominal obesity with metabolic disorders, abdominal obesity with relative GH deficiency, metabolic syndrome or syndrome X, lipohypertrophy, lipoatrophy, lipodystrophy (e.g., HIV-associated lipodystrophy syndrome), dyslipidemia, hypertriglyceridemia), (3) improving anabolism in catabolic/wasting conditions, such as those observed in acute or chronic renal failure (e.g., acute or chronic renal failure wasting), chronic heart failure (e.g., chronic heart failure wasting), chronic obstructive pulmonary disease (COPD), cystic fibrosis (e.g., cystic fibrosis wasting in adults), frailty, burns, infections (sepsis), muscular dystrophy, congestive heart failure, neurodegenerative conditions (Alzheimer's, pre-Alzheimer's syndromes, amyotrophic lateral sclerosis (ALS), AIDS, protein malnutrition following long-term corticosteroid therapy, following non-union bone fracture, hip fracture, trauma, or major surgery (post-surgical problems), osteoporosis, long-term immobilization, cancer-related cachexia, sarcopenia (e.g., age-related sarcopenia), GI malabsorption (Short Bowel Syndrome (SBS), Crohn's disease) particularly in elderly subjects, for example to increase muscle mass and/or function, (4) improving immune function or reconstitution of immunodeficient states (e.g., T-cell immunodeficiencies) such as that associated with aging, HIV infection/AIDS or following high-dose chemotherapy and/or radiotherapy (in HIV-infected and cancer patients), (5) altering a lipid parameter ((a) decreasing cholesterol; (b) decreasing non-HDL cholesterol; (c) decreasing triglycerides; and/or (d) decreasing the ratio of total cholesterol/HDL cholesterol); (6) altering a body composition parameter ((a) increasing lean body mass; (b) decreasing trunk fat; (c) decreasing visceral fat; (d) decreasing abdominal girth; (e) decreasing visceral adipose tissue (VAT); and/or (f) decreasing the VAT/subcutaneous adipose tissue (SAT) ratio), (7) enhancing fertility or treating infertility (in women), treating lactation failure, (8) treating GH deficiency (e.g., GH deficiency with abdominal obesity), providing GH replacement therapy, e.g., in adults, treating idiopathic short stature (ISS) (9) treating GRF receptor-related tumors, (10) treating hypothalamic pituitary dwarfism, (11) improving wound healing, (12) treating burns, (13) treating acute/chronic debilitating illness or infection, and/or (14) preventing/treating a condition characterized by deficient or decreased bone formation (e.g., osteoporosis); the method comprising administering an effective amount of the above-mentioned GRF analog or pharmaceutically acceptable salt thereof or a composition comprising the above-mentioned GRF analog or pharmaceutically acceptable salt thereof (e.g., together with a pharmaceutically acceptable carrier/excipient), to a subject in need thereof.

In other aspects, the present invention provides a use of the above-mentioned GRF analog or pharmaceutically acceptable salt thereof or a composition comprising the above-mentioned GRF analog or pharmaceutically acceptable salt thereof (e.g., together with a pharmaceutically acceptable carrier/excipient), for improving, preventing and/or treating the conditions, diseases or disorders noted above, or for the preparation/manufacture of a medicament for improving, preventing and/or treating the conditions, diseases or disorders noted above. In other aspects, the present invention provides the above-mentioned GRF analog or pharmaceutically acceptable salt thereof or a composition comprising the above-mentioned GRF analog or pharmaceutically acceptable salt thereof (e.g., together with a pharmaceutically acceptable carrier/excipient) for use in improving, preventing and/or treating the conditions, diseases or disorders noted above, or for the preparation/manufacture of a medicament for improving, preventing and/or treating the conditions, diseases or disorders noted above.

The term "treatment" or "treating" as used herein, is defined as the application or administration of the above-mentioned GRF analog or pharmaceutically acceptable salt thereof or the above-mentioned composition to a subject, or application or administration of the above-mentioned GRF analog or pharmaceutically acceptable salt thereof or the above-mentioned composition to an isolated tissue or cell line from a subject, who has a disorder, a disease, a symptom of disorder or disease, with the purpose to cure, heal, alleviate, relieve, alter, remedy, ameliorate, improve, reduce the progression or affect the disorder/disease and/or the symptoms of disorder/disease. In an embodiment, the treatment results in no or substantially no effect on blood glucose control (e.g., no clinically significant effects).

The term "prevention" or "preventing" as used herein, is defined as the application or administration of the above-mentioned GRF analog or pharmaceutically acceptable salt thereof or the above-mentioned composition to a subject, or application or administration of the above-mentioned GRF analog or pharmaceutically acceptable salt thereof or the above-mentioned composition to an isolated tissue or cell line from a subject, who has a predisposition toward a disorder/disease or who is at risk of developing the disorder/disease, with the purpose to prevent or delay the onset of the disease/disorder or of the symptoms, or reduce the severity of the disease/disorder or of the symptoms, when administered prior to the onset/appearance of the disease/disorder or of the symptoms.

An "effective amount" refers to an amount effective, at dosages and for periods of time necessary, to achieve the desired biological activity (e.g. inducing GH secretion) and/or the prophylactic/therapeutic result (e.g., prevention and/or treatment of the diseases/disorders noted above). A "therapeutically effective amount" refers to an effective amount in the context of therapy; a "prophylactically effective amount" refers to an effective amount in the context of prophylaxis. An effective amount of a compound of the invention may vary according to factors such as the disease state, age, sex, and weight of the individual, and the ability of the compound to elicit a desired response in the individual. Dosage regimens may be adjusted to provide the optimum prophylactic/therapeutic response. An effective amount is also one in which any toxic or detrimental effects of the compound are outweighed by the prophylactic/therapeutic beneficial effects. For any particular subject, specific dosage regimens may be adjusted over time according to the individual need and the professional judgment of the person administering or supervising the administration of the compositions. In an embodiment, the GRF analog is administered at a daily dose of about 0.01 mg to about 30 mg, in a further embodiment of about 0.1 mg to about 20 or 25 mg, in a further embodiment of about 0.5 mg to about 20 mg, in a further embodiment at a daily dose of about 1 mg to about 20 mg.

The GRF analogs or pharmaceutically acceptable salts thereof or composition of the present invention may be administered, or may be for administration, by any conventional route, such as intravenous, oral, transdermal, intraperitoneal, subcutaneous, mucosal, intramuscular, intranasal, intrapulmonary, parenteral or topical. In an embodiment, the GRF analog or pharmaceutically acceptable salt thereof is administered or is for administration by a subcutaneous route. In another embodiment, the GRF analog or pharmaceutically acceptable salt thereof is administered or is for administration by a transdermal route (e.g., using transdermal delivery systems such as transdermal patches). Accordingly, in another aspect, the present invention provides a transdermal delivery system, such as a transdermal patch, comprising the above-mentioned GRF analog (or pharmaceutically acceptable salt thereof) or pharmaceutical composition. Methods and systems for transdermal delivery are well known in the art and are described, for example, in *Transdermal Drug Delivery*, Second Edition, Marcel Dekker Inc., New York, 2003 and *Transdermal and Topical Drug Delivery*, Adrian C Williams, Pharmaceutical Press, 2003. In another embodiment, the GRF analog or pharmaceutically acceptable salt thereof is administered or is for administration by the oral route. In an embodiment, the GRF analog or pharmaceutically acceptable salt thereof is administered or is for administration by a nasal route.

In an embodiment, the above-mentioned prevention and/or treatment comprises administration of the above-mentioned GRF analogs or pharmaceutically acceptable salts thereof or compositions, in combination with one or more additional active/therapeutic agents. The combination of prophylactic/therapeutic agents and/or compositions may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent(s) currently used to prevent or treat the disorder in question.

As used herein, the terms "subject" or "patient" are taken to mean warm blooded animals such as mammals, for example, cats, dogs, mice, guinea pigs, horses, bovine cows, sheep and humans. In an embodiment, the subject is a mammal. In a further embodiment, the above-mentioned subject is a human.

The present invention is illustrated in further details by the following non-limiting examples.

The following abbreviations are used herein:

| | |
|---|---|
| DMF: | N,N-Dimethylformamide |
| DIEA: | Diisopropylethylamine |
| HCTU: | [2-(6-Chloro-1H-benzotriazole-1-yl)-1,1,3,3-tetramethylaminium hexafluorophosphate] |
| COMU: | (1-Cyano-2-ethoxy-2-oxoethylidenaminooxy) dimethylamino-morpholino-carbenium hexafluorophosphate (COMU) |
| TFA: | Trifluoroacetic acid |
| MALDI-TOF: | Matrix Assisted Laser Desorption/Ionization Mass Spectrometry. |
| HPLC: | High Performance Liquid Chromatography |
| BHA: | Benzhydrylamine resin |
| Pbf: | 2,2,4,6,7-Pentamethyldihydrobenzo-furane-5-sulfonyl |
| Boc: | t-Butoxycarbonyl |
| t-Bu: | t-Butyl |
| Trt: | Trityl |
| Aib: | α-aminoisobutyric acid |
| O: | L-ornithine |
| Ac: | acetyl |
| HoArg: | L-Homoarginine |
| HoSer: | L-Homoserine |
| a: | D-alanine |
| r: | D-arginine |

Throughout the instant application, naturally occurring amino acids are designated interchangeably using the one or three letter codes (see Table I below for correspondence between them).

TABLE I

Amino acids, one and three letter codes

| Amino acid | Three letter code | One letter code |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Example 1

Materials and Methods

Synthesis and Preparation of GRF Analogs.
Solid Phase Synthesis

The GRF analogs of the present invention were made using a manual or an automatic solid phase peptide synthesis approach using fluorenylmethoxycarbonyl-protected alpha-amino acids with appropriate side-chain protection and Benzhydrylamine (BHA) resin (BACHEM AG) with a loading of 0.75 mmol/g. Before the coupling of amino acids, 6-aminohexanoic acid and Rink linker were coupled to the resin, the Fmoc-[9H-fluoren-9-ylmethoxycarbonyl] protected amino acid were then coupled using [2-(6-Chloro-1H-benzotriazole-1-yl)-1,1,3,3-tetramethylaminium hexafluorophosphate] (HCTU) or (1-Cyano-2-ethoxy-2-oxoethylidenaminooxy) dimethylamino-morpholino-carbenium hexafluorophosphate (COMU), and diisopropylethylamine (DIEA) in N,N-Dimethylformamide (DMF) for about 1 hour. Fmoc deprotection was performed using 20% (v/v) piperidine in DMF for about 0.5 hour. A general procedure for N-capping the peptides of the invention with acetyl was performed using acetic anhydride and DIEA. After completion of synthesis, peptides were cleaved from the solid phase support with simultaneous side-chain deprotection. Crude linear peptides were further purified by preparative RP-HPLC on C18-columns using acetonitrile gradient in 0.1% Trifluoroacetic acid (TFA). The peptides were vacuum-dried to remove acetonitrile and lyophilized from 0.1% TFA. Purity was assessed by analytical High Performance Liquid Chromatography (HPLC) and masses were determined by Matrix Assisted Laser Desorption/ionisation Mass Spectrometry (MALDI-TOF MS) analysis using a Voyager™ instrument (PerSeptive Biosystems Inc.).

Determination of the Activity of the GRF Analogs of the Present Invention.

Alkaline Phosphatase (AP) Assay

The activity of representative GRF peptides was tested on baby hamster kidney (BHK) cells stably transfected to express the human GRF receptor and an alkaline phosphatase reporter gene. Cells were cultured 24 hours before stimulation, in 96-well plates, at a concentration of $0.5 \times 10^5$ cells/well. Before stimulation, cells were washed twice with DPBS and incubated 10-30 min in assay buffer (DMEM without phenol red supplemented with 20 mM HEPES and 1% heat inactivated fetal bovine serum (FBS). The dose response curve of the GRF peptides was done for 24 hrs with concentrations of peptides from $10^{-5}$ M to $10^{-11}$ M. Supernatant was collected and analysis of alkaline phosphatase levels was performed using the Alkaline Phosphatase detection kit from Applied Biosystems.

GRF Analog Administration and Sample Collection in Mice

CD-1 mice (female, weighting from 20 to 25 g) were obtained from Charles River Inc. Animals were used according to a protocol of the Animal Care Committee along with the principles of the Guide for the Care and Use of Experimental Animals of the Canadian Council on Animal Care. The animals were maintained on standard laboratory chow under a 12:12 light:dark cycle. They were kept in groups of 4 mice per cage.

At the day of the experiment, mice received a subcutaneous injection of GRF analog (10 µg/mouse dissolved in 20 mM sodium acetate (AcONa)+5% mannitol at pH 5). 10 minutes after injection, the mice were anesthezied with isolufrane. Blood samples (500 µl) were obtained by intra-cardiac puncture. Blood was placed into microtainer pre-treated with $K_3$EDTA and immediately centrifuged at 13,000 RPM in a desktop centrifuge for 2 minutes. The plasma was collected and placed into a screwcap Eppendorf™ tube and quick frozen in liquid nitrogen. The samples were then kept at −80° C. until assayed. Determination of GH levels was performed as described below.

GRF Analog Administration and Sample Collection in Rats

Sprague-Dawley rats (female, weighting from 250 to 300 g) were obtained from Charles River Inc. Animals were used according to a protocol of the Animal Care Committee along with the principles of the Guide for the Care and Use of Experimental Animals of the Canadian Council on Animal Care. The animals were maintained on standard laboratory chow under a 12:12 light:dark cycle. They were kept in groups of 4 rats per cage.

The animals were anesthetized with isoflurane 2.5%. A mid-section opening was made in the neck to expose the carotid artery. The carotid artery was canulated with polypropylene tubing (PE-50) to allow blood withdrawal. After surgical preparation, rats received a subcutaneous injection of GRF analog (10 µg/rat dissolved in 20 mM AcONa+5% mannitol at pH 5). For pharmacodynamics studies, blood samples (400 µL) were collected from 4 to 8 animals per group per time point. Blood samples (400 µl) were collected via the carotid catheter at 0, 10, 20, 30, 45 and 60 minutes after drug injection. Blood was placed into microtainer pre-treated with $K_3$EDTA and immediately centrifuged at 13,000 RPM in a desktop centrifuge for 2 minutes. The plasma was collected and placed into a screw cap Eppendorf™ and quick frozen in liquid nitrogen. The samples were then kept at −80° C. until assayed. Determination of GH levels was performed as described below.

Determination of GH Levels in Plasma Samples

Rat and mouse plasma samples were vortexed carefully and centrifuged at 9,000 RPM for 2 min at 4° C. The dosage of GH levels was performed using the Rat/Mouse Growth Hormone ELISA kit from Millipore (Cat. # EZRMGH-45K). Sample supernatants were first diluted 20-fold with the GH ELISA assay buffer, and 10 µl of this dilution was added to the ELISA plate with 90 µl of GH EIA assay buffer. The remaining of the procedure was performed according to the manufacturer's instructions, and the data obtained were analyzed using GraphPad Prism™ software.

Example 2

GHRHr Agonist Activity of the GRF Analogs

The in vitro activity of representative GRF analogs was tested on baby hamster kidney (BHK) cells expressing human GHRHr. The results are presented in Table II.

TABLE II $EC_{50}$ of representative GRF analogs described herein as assessed by alkaline phosphatase (AP) induction

| Sequence | $EC_{50}$ (nM) | SD | N |
|---|---|---|---|
| Ac-Y-A-D-A-I-F-T-D-S-Y-R-K-V-L-A-Q-L-S-A-R-K-L-L-Q-D-I-L-S-R-$NH_2$ (SEQ ID NO: 43) ($GRF_{(1-29)}$ analog with N-terminal acetylation, C-terminal amidation, Asn(8) substituted with Asp(8), Gly(15) substituted with Ala(15) and Met(27) substituted with Leu(27)) | 0.25 | 0.78 | 13 |
| Trans-3-hexenoyl-Y-A-D-A-I-F-T-D-S-Y-R-K-V-L-A-Q-L-S-A-R-Q-D-I-M-S-R-$NH_2$ (SEQ ID NO: 44) | 9.73 | 1.41 | 3 |
| Trans-3-hexenoyl-Y-A-D-A-I-F-T-D-S-Y-R-K-V-L-A-Q-L-S-A-R-Q-D-I-L-A-R-$NH_2$ (SEQ ID NO: 45) | 7.55 | 4.09 | 3 |
| Trans-3-hexenoyl-Y-A-D-A-I-F-T-D-S-Y-R-K-V-L-A-Q-L-S-A-R-Q-D-I-L-S-r-$NH_2$ (SEQ ID NO: 46) | 15.1 | 4.38 | 3 |
| Trans-3-hexenoyl-Y-A-D-A-I-F-T-D-S-Y-R-K-V-L-A-Q-L-K-A-R-Q-D-I-L-A-R-$NH_2$ (SEQ ID NO: 20) | 0.98 | 0.50 | 3 |
| Y-a-D-A-I-F-T-D-S-Y-R-K-V-L-A-Q-L-K-A-R-Q-D-I-L-S-r-$NH_2$ (SEQ ID NO: 21) | 2.47 | 0.81 | 2 |
| Y-a-D-A-I-F-T-D-S-Y-R-K-V-L-A-Q-L-K-A-R-Q-D-I-L-aib-R-$NH_2$ (SEQ ID NO: 22) | 0.72 | 0.00 | 1 |
| Y-a-D-A-I-F-T-D-S-Y-R-K-V-L-A-Q-L-O-A-R-Q-D-I-L-S-r-$NH_2$ (SEQ ID NO: 23) | 1.14 | 0.46 | 3 |
| Trans-3-hexenoyl-Y-A-D-A-I-F-T-D-S-Y-R-K-V-L-A-Q-L-O-A-R-Q-D-I-L-S-r-$NH_2$ (SEQ ID NO: 24); | 1.18 | 0.90 | 3 |
| Y-a-D-A-I-F-T-D-S-Y-R-K-V-L-A-Q-L-K-A-R-Q-D-L-L-S-r-$NH_2$ (SEQ ID NO: 25) | 2.35 | 0.00 | 1 |
| Trans-3-hexenoyl-Y-A-D-A-I-F-T-D-S-Y-R-K-V-L-A-Q-L-K-A-R-Q-D-I-L-A-R-A-A-R-$NH_2$ (SEQ ID NO: 26) | 0.13 | 0.00 | 1 |
| Trans-3-hexenoyl-Y-A-D-A-I-F-T-D-S-Y-R-K-V-L-A-Q-L-S-A-R-Q-D-I-L-A-R-A-A-R-A-A-R-$NH_2$ (SEQ ID NO: 27) | 0.19 | 0.07 | 3 |
| Y-a-D-A-I-F-T-D-S-Y-R-K-V-L-A-Q-L-K-A-R-Q-D-I-L-A-R-A-A-R-A-A-R-$NH_2$ (SEQ ID NO: 28) | 0.11 | 0.14 | 14 |
| Y-a-D-A-I-F-T-D-S-Y-R-K-V-L-A-Q-L-K-L-R-Q-D-I-L-A-R-A-A-R-A-A-R-$NH_2$ (SEQ ID NO: 29) | 0.08 | 0.00 | 1 |
| Y-a-D-A-I-F-T-D-S-Y-R-K-V-L-A-Q-L-K-A-R-Q-D-L-L-A-R-A-A-R-A-A-R-$NH_2$ (SEQ ID NO: 30) | 0.18 | 0.03 | 3 |
| Trans-3-hexenoyl-Y-A-D-A-I-F-T-D-S-Y-R-K-V-L-A-Q-L-K-A-R-Q-D-I-L-A-R-A-A-R-A-A-R-$NH_2$ (SEQ ID NO: 31) | 0.10 | 0.04 | 4 |

TABLE II-continued

EC$_{50}$ of representative GRF analogs described herein as assessed by alkaline phosphatase (AP) induction

| Sequence | EC$_{50}$ (nM) | SD | N |
|---|---|---|---|
| Trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32) | 0.11 | 0.07 | 4 |
| Y-S-D-A-I-F-T-D-S-Y-R-K-V-L-A-Q-L-K-A-R-Q-D-I-L-A-R-A-A-R-A-A-R-NH$_2$ (SEQ ID NO: 33) | 0.25 | 0.00 | 1 |
| Y-G-D-A-I-F-T-D-S-Y-R-K-V-L-A-Q-L-K-A-R-Q-D-I-L-A-R-A-A-R-A-A-R-NH$_2$ (SEQ ID NO: 34) | 0.20 | 0.04 | 4 |
| Y-L-D-A-I-F-T-D-S-Y-R-K-V-L-A-Q-L-K-A-R-Q-D-I-L-A-R-A-A-R-A-A-R-NH$_2$ (SEQ ID NO: 35) | 2.52 | 0.67 | 2 |
| Y-G-D-A-I-F-T-D-S-Y-R-K-V-L-A-Q-L-K-A-R-Q-D-I-L-A-R-A-A-R-A-A-R-HoSer-NH$_2$ (SEQ ID NO: 36) | 0.20 | 0.03 | 5 |
| Y-a-D-A-I-F-T-D-S-Y-R-K-V-L-A-Q-L-K-A-R-Q-D-I-L-A-R-A-A-R-A-A-R-HoSer-NH$_2$ (SEQ ID NO: 37) | 0.20 | 0.00 | 1 |

Ac: acetyl
a: D-alanine
r: D-arginine
Aib: amino isobutyric acid
O: L-ornithine
HoSer: L-homoserine
SD: standard deviation
N: number of experiments Example 3

GH-Releasing Properties of the GRF Analogs

The GRF analogs described herein were tested for their ability to induce GH release in female mice and rats. GH release induced by an analog of native GRF$_{(1-29)}$ peptide having an N-terminal acetylation, C-terminal amidation, Asn(8) substituted with Asp(8), Gly(15) substituted with Ala(15) and Met(27) substituted with Leu(27) (SEQ ID NO: 43), which is more active than native GRF$_{(1-29)}$, was also measured in parallel for comparison. The data are presented in Tables III (mice) and IV-V (rats).

TABLE III

Growth Hormone Secretion in female mice in response to administration of representative GRF analogs described herein

| Sequence | GH levels 10 min (ng/ml) | SD | P value | N |
|---|---|---|---|---|
| Ac-Y-A-D-A-I-F-T-D-S-Y-R-K-V-L-A-Q-L-S-A-R-K-L-L-Q-D-I-L-S-R-NH$_2$ (SEQ ID NO: 43) (GRF$_{(1-29)}$ analog with N-terminal acetylation, C-terminal amidation, Asn(8) substituted with Asp(8), Gly(15) substituted with Ala(15) and Met(27) substituted with Leu(27) | 277 | 57.4 | NAP | 7 |
| Trans-3-hexenoyl-Y-A-D-A-I-F-T-D-S-Y-R-K-V-L-A-Q-L-S-A-R-Q-D-I-M-S-R-NH$_2$ (SEQ ID NO: 44) | 15.2 | 13.2 | * | 4 |
| Trans-3-hexenoyl-Y-A-D-A-I-F-T-D-S-Y-R-K-V-L-A-Q-L-S-A-R-Q-D-I-L-A-R-NH$_2$ (SEQ ID NO: 45) | 102.1 | 72.3 | * | 4 |
| Trans-3-hexenoyl-Y-A-D-A-I-F-T-D-S-Y-R-K-V-L-A-Q-L-S-A-R-Q-D-I-L-S-r-NH$_2$ (SEQ ID NO: 46) | 10.6 | 3.6 | * | 4 |
| Trans-3-hexenoyl-Y-A-D-A-I-F-T-D-S-Y-R-K-V-L-A-Q-L-K-A-R-Q-D-I-L-A-R-NH$_2$ (SEQ ID NO: 20) | 307.7 | 48.1 | * | 4 |
| Y-a-D-A-I-F-T-D-S-Y-R-K-V-L-A-Q-L-K-A-R-Q-D-I-L-S-r-NH$_2$ (SEQ ID NO: 21) | 104.4 | 32.6 | * | 9 |
| Y-a-D-A-I-F-T-D-S-Y-R-K-V-L-A-Q-L-K-A-R-Q-D-I-L-aib-R-NH$_2$ (SEQ ID NO: 22) | 249.1 | 35.0 | * | 4 |
| Y-a-D-A-I-F-T-D-S-Y-R-K-V-L-A-Q-L-O-A-R-Q-D-I-L-S-r-NH$_2$ (SEQ ID NO: 23) | 269.9 | 123.4 | * | 11 |
| Trans-3-hexenoyl-Y-A-D-A-I-F-T-D-S-Y-R-K-V-L-A-Q-L-O-A-R-Q-D-I-L-S-r-NH$_2$ (SEQ ID NO: 24); | 332.6 | 118.4 | * | 4 |

TABLE III-continued

Growth Hormone Secretion in female mice in response to administration of representative GRF analogs described herein

| Sequence | GH levels 10 min (ng/ml) | SD | P value | N |
|---|---|---|---|---|
| Y-a-D-A-I-F-T-D-S-Y-R-K-V-L-A-Q-L-K-A-R-Q-D-L-L-S-r-NH$_2$ (SEQ ID NO: 25) | 144.1 | 50.1 | * | 4 |
| Trans-3-hexenoyl-Y-A-D-A-I-F-T-D-S-Y-R-K-V-L-A-Q-L-K-A-R-Q-D-I-L-A-R-A-A-R-NH$_2$ (SEQ ID NO: 26) | 484.6 | 105.7 | * | 4 |
| Trans-3-hexenoyl-Y-A-D-A-I-F-T-D-S-Y-R-K-V-L-A-Q-L-S-A-R-Q-D-I-L-A-R-A-A-R-A-A-R-NH$_2$ (SEQ ID NO: 27) | 323.6 | 146.6 | * | 4 |
| Y-a-D-A-I-F-T-D-S-Y-R-K-V-L-A-Q-L-K-A-R-Q-D-I-L-A-R-A-A-R-A-A-R-NH$_2$ (SEQ ID NO: 28) | 449.7 | 169.8 | * | 8 |
| Y-a-D-A-I-F-T-D-S-Y-R-K-V-L-A-Q-L-K-L-R-Q-D-I-L-A-R-A-A-R-A-A-R-NH$_2$ (SEQ ID NO: 29) | 457.7 | 102.9 | * | 4 |
| Y-a-D-A-I-F-T-D-S-Y-R-K-V-L-A-Q-L-K-A-R-Q-D-L-L-A-R-A-A-R-A-A-R-NH$_2$ (SEQ ID NO: 30) | 493.3 | 187.0 | * | 8 |
| Trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31) | 563.6 | 259.6 | * | 8 |
| Trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32) | 401.6 | 200.9 | * | 8 |

Ac: acetyl
a: D-alanine
r: D-arginine
Aib: amino isobutyric acid
O: L-ornithine
SD: standard deviation
NAP: Not applicable
*: value statistically different from value obtained with SEQ ID NO: 43 according to One-way Anova test, Dunnett comparison
N: number of animals

TABLE IV

Cumulative rat Growth Hormone secretion in female rats in response to administration of representative GRF analogs described herein, as determined by GH Area Under the curve (AUC, GH concentration over time).

| Sequence | Mean AUC | SD | P value | N |
|---|---|---|---|---|
| Ac-Y-A-D-A-I-F-T-D-S-Y-R-K-V-L-A-Q-L-S-A-R-K-L-L-Q-D-I-L-S-R-NH$_2$ (SEQ ID NO: 43) (GRF$_{(1-29)}$ analog with N-terminal acetylation, C-terminal amidation, Asn(8) substituted with Asp(8), Gly(15) substituted with Ala(15) and Met(27) substituted with Leu(27)) | 2128 | 347.70 | NAP | 4 |
| Trans-3-hexenoyl-Y-A-D-A-I-F-T-D-S-Y-R-K-V-L-A-Q-L-S-A-R-Q-D-I-M-S-R-NH$_2$ (SEQ ID NO: 44) | 984 | 284 | NS | 4 |
| Trans-3-hexenoyl-Y-A-D-A-I-F-T-D-S-Y-R-K-V-L-A-Q-L-S-A-R-Q-D-I-L-A-R-NH$_2$ (SEQ ID NO: 45) | 1953 | 462 | NS | 4 |
| Trans-3-hexenoyl-Y-A-D-A-I-F-T-D-S-Y-R-K-V-L-A-Q-L-S-A-R-Q-D-I-L-S-r-NH$_2$ (SEQ ID NO: 46) | 1453 | 372 | NS | 4 |
| Trans-3-hexenoyl-Y-A-D-A-I-F-T-D-S-Y-R-K-V-L-A-Q-L-K-A-R-Q-D-I-L-A-R-NH$_2$ (SEQ ID NO: 20) | 966 | 109 | NS | 4 |
| Y-a-D-A-I-F-T-D-S-Y-R-K-V-L-A-Q-L-K-A-R-Q-D-I-L-S-r-NH$_2$ (SEQ ID NO: 21) | 3130 | 1250 | NS | 8 |
| Trans-3-hexenoyl-Y-A-D-A-I-F-T-D-S-Y-R-K-V-L-A-Q-L-K-A-R-Q-D-I-L-A-R-A-A-R-NH$_2$ (SEQ ID NO: 26) | 8880 | 3110 | * | 4 |
| Trans-3-hexenoyl-Y-A-D-A-I-F-T-D-S-Y-R-K-V-L-A-Q-L-S-A-R-Q-D-I-L-A-R-A-A-R-A-A-R-NH$_2$ (SEQ ID NO: 27) | 8350 | 3620 | * | 4 |

TABLE IV-continued

Cumulative rat Growth Hormone secretion in female rats in response to administration of representative GRF analogs described herein, as determined by GH Area Under the curve (AUC, GH concentration over time).

| Sequence | Mean AUC | SD | P value | N |
|---|---|---|---|---|
| Y-a-D-A-I-F-T-D-S-Y-R-K-V-L-A-Q-L-K-A-R-Q-D-I-L-A-R-A-A-R-A-A-R-NH$_2$ (SEQ ID NO: 28) | 17633 | 5338 | * | 8 |
| Y-a-D-A-I-F-T-D-S-Y-R-K-V-L-A-Q-L-K-L-R-Q-D-I-L-A-R-A-A-R-A-A-R-NH$_2$ (SEQ ID NO: 29) | 9442 | 541 | * | 4 |
| Y-a-D-A-I-F-T-D-S-Y-R-K-V-L-A-Q-L-K-A-R-Q-D-L-L-A-R-A-A-R-A-A-R-NH$_2$ (SEQ ID NO: 30) | 12282 | 3226 | * | 8 |
| Trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31) | 9093 | 2606 | * | 8 |
| Trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32) | 10500 | 5282 | * | 8 |
| Y-S-D-A-I-F-T-D-S-Y-R-K-V-L-A-Q-L-K-A-R-Q-D-I-L-A-R-A-A-R-A-A-R-NH$_2$ (SEQ ID NO: 33) | 12467 | 743 | NS | 8 |
| Y-G-D-A-I-F-T-D-S-Y-R-K-V-L-A-Q-L-K-A-R-Q-D-I-L-A-R-A-A-R-A-A-R-NH$_2$ (SEQ ID NO: 34) | 11046 | 5162 | * | 4 |
| Y-L-D-A-I-F-T-D-S-Y-R-K-V-L-A-Q-L-K-A-R-Q-D-I-L-A-R-A-A-R-A-A-R-NH$_2$ (SEQ ID NO: 35) | 9144 | 4865 | NS | 4 |
| Y-G-D-A-I-F-T-D-S-Y-R-K-V-L-A-Q-L-K-A-R-Q-D-I-L-A-R-A-A-R-A-A-R-HoSer-NH$_2$ (SEQ ID NO: 36) | 6211 | 3365 | NS | 4 |
| Y-a-D-A-I-F-T-D-S-Y-R-K-V-L-A-Q-L-K-A-R-Q-D-I-L-A-R-A-A-R-A-A-R-HoSer-NH$_2$ (SEQ ID NO: 37) | 14757 | 8617 | * | 3 |

Ac: acetyl
a: D-alanine
r: D-arginine
Aib: amino isobutyric acid
O: L-ornithine
HoSer: L-homoserine
SD: standard deviation
NAP: Not applicable
NS: value not statistically different from value obtained with SEQ ID NO: 43 according to One-way Anova test, Dunnett comparison
*: value statistically different from value obtained with SEQ ID NO: 43 according to One-way Anova test, Dunnett comparison
N: number of animals

TABLE V $C_{max}$ of Growth Hormone secretion in female rats in response to administration of representative GRF analogs described herein (GH concentration over time)

| Sequence | Mean $C_{max}$ (ng/ml) | SD | P value | N |
|---|---|---|---|---|
| Ac-Y-A-D-A-I-F-T-D-S-Y-R-K-V-L-A-Q-L-S-A-R-K-L-L-Q-D-I-L-S-R-NH$_2$ (SEQ ID NO: 43) (GRF$_{(1-29)}$ analog with N-terminal acetylation, C-terminal amidation, Asn(8) substituted with Asp(8), Gly(15) substituted with Ala(15) and Met(27) substituted with Leu(27) | 83.6 | 14.1 | NAP | 4 |
| Trans-3-hexenoyl-Y-A-D-A-I-F-T-D-S-Y-R-K-V-L-A-Q-L-S-A-R-Q-D-I-M-S-R-NH$_2$ (SEQ ID NO: 44) | 44.2 | 24.2 | NS | 4 |
| Trans-3-hexenoyl-Y-A-D-A-I-F-T-D-S-Y-R-K-V-L-A-Q-L-S-A-R-Q-D-I-L-A-R-NH$_2$ (SEQ ID NO: 45) | 78.8 | 16.0 | NS | 4 |
| Trans-3-hexenoyl-Y-A-D-A-I-F-T-D-S-Y-R-K-V-L-A-Q-L-S-A-R-Q-D-I-L-S-r-NH$_2$ (SEQ ID NO: 46) | 57.3 | 27.5 | NS | 4 |

TABLE V-continued $C_{max}$ of Growth Hormone secretion in female rats in response to administration of representative GRF analogs described herein (GH concentration over time)

| Sequence | Mean $C_{max}$ (ng/ml) | SD | P value | N |
|---|---|---|---|---|
| Trans-3-hexenoyl-Y-A-D-A-I-F-T-D-S-Y-R-K-V-L-A-Q-L-K-A-R-Q-D-I-L-A-R-NH$_2$ (SEQ ID NO: 20) | 31.7 | 7.6 | NS | 4 |
| Y-a-D-A-I-F-T-D-S-Y-R-K-V-L-A-Q-L-K-A-R-Q-D-I-L-S-r-NH$_2$ (SEQ ID NO: 21) | 135.9 | 73.0 | NS | 8 |
| Trans-3-hexenoyl-Y-A-D-A-I-F-T-D-S-Y-R-K-V-L-A-Q-L-K-A-R-Q-D-I-L-A-R-A-A-R-NH$_2$ (SEQ ID NO: 26) | 468.1 | 147.9 | * | 4 |
| Trans-3-hexenoyl-Y-A-D-A-I-F-T-D-S-Y-R-K-V-L-A-Q-L-S-A-R-Q-D-I-L-A-R-A-A-R-A-A-R-NH$_2$ (SEQ ID NO: 27) | 455.6 | 210.4 | * | 4 |
| Y-a-D-A-I-F-T-D-S-Y-R-K-V-L-A-Q-L-K-A-R-Q-D-I-L-A-R-A-A-R-A-A-R-NH$_2$ (SEQ ID NO: 28) | 806.2 | 240.3 | * | 8 |
| Y-a-D-A-I-F-T-D-S-Y-R-K-V-L-A-Q-L-K-L-R-Q-D-I-L-A-R-A-A-R-A-A-R-NH$_2$ (SEQ ID NO: 29) | 466.7 | 124.3 | * | 4 |
| Y-a-D-A-I-F-T-D-S-Y-R-K-V-L-A-Q-L-K-A-R-Q-D-L-L-A-R-A-A-R-A-A-R-NH$_2$ (SEQ ID NO: 30) | 664.1 | 168.7 | * | 8 |
| Trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31) | 459.9 | 175.5 | * | 8 |
| Trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32) | 514.8 | 241.1 | * | 8 |
| Y-S-D-A-I-F-T-D-S-Y-R-K-V-L-A-Q-L-K-A-R-Q-D-I-L-A-R-A-A-R-A-A-R-NH$_2$ (SEQ ID NO: 33) | 499.0 | 12.7 | NS | 8 |
| Y-G-D-A-I-F-T-D-S-Y-R-K-V-L-A-Q-L-K-A-R-Q-D-I-L-A-R-A-A-R-A-A-R-NH$_2$ (SEQ ID NO: 34) | 539.7 | 236.3 | NS | 4 |
| Y-L-D-A-I-F-T-D-S-Y-R-K-V-L-A-Q-L-K-A-R-Q-D-I-L-A-R-A-A-R-A-A-R-NH$_2$ (SEQ ID NO: 35) | 376.9 | 128.5 | NS | 4 |
| Y-G-D-A-I-F-T-D-S-Y-R-K-V-L-A-Q-L-K-A-R-Q-D-I-L-A-R-A-A-R-A-A-R-HoSer-NH$_2$ (SEQ ID NO: 36) | 373.5 | 207.4 | NS | 4 |
| Y-a-D-A-I-F-T-D-S-Y-R-K-V-L-A-Q-L-K-A-R-Q-D-I-L-A-R-A-A-R-A-A-R-HoSer-NH$_2$ (SEQ ID NO: 37) | 594.6 | 145.3 | NS | 3 |

Ac: acetyl
a: D-alanine
r: D-arginine
Aib: amino isobutyric acid
O: L-ornithine
HoSer: L-homoserine
SD: standard deviation
NAP: Not applicable
NS: value not statistically different from value obtained with SEQ ID NO: 43 according to One-way Anova test, Dunnett comparison
*: value statistically different from value obtained with SEQ ID NO: 43 according to One-way Anova test, Dunnett comparison
N: number of animals Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

The invention claimed is:

1. A growth hormone releasing factor (GRF) analog comprising a domain of formula (I) (SEQ ID NO: 1):

X1-X2-Asp-Ala-Ile-Phe-Thr-X8-X9-Tyr-X11-X12-X13-Leu-X15-Gln-Leu-X18-X19-Arg-Gln-X22-X23-X24-X25-X26-X27-X28-X29-X30-X31-X32-X33(1)

wherein:
X1 is Tyr or H is;
X2 is Ala, D-Ala, Ser, Leu, α-aminoisobutyric acid (Aib), Val or Gly;
X8 is Asn, Asp, Ala, Gln, Ser or Aib;
X9 is Ser, Asp or Ala;
X11 is Arg or L-Homoarginine (HoArg);
X12 is Lys, L-Ornithine (Orn) or HoArg;
X13 is Val or Ile;
X15 is Gly or Ala;
X18 is Lys, L-Ornithine, L-2,4-diaminobutyric acid, L-2,3-diaminopropionic acid, or Ser;
X19 is Ala or Leu
X22 is Asp or Glu;
X23 is Ile or Leu;
X24 is Met, Ile, Nle or Leu;
X25 is Ser, Asn, Aib or Ala;
X26 is Arg, D-Arg, HoArg or Lys;
X27 is Ala or is absent;
X28 is Ala or is absent;
X29 is Arg or is absent;
X30 is Ala or is absent;
X31 is Ala or is absent;
X32 is Arg or is absent;
X33 is L-Homoserine (HoSer) or is absent;
and wherein if X18 is Ser, X27 to X32 or X27 to X33 are present,
or a pharmaceutically acceptable salt thereof.

2. The GRF analog of claim 1, wherein X1 is Tyr.
3. The GRF analog of claim 1, wherein X2 is Ala or D-Ala.
4. The GRF analog of claim 1, wherein X8 is Ala or Asp.
5. The GRF analog of claim 1, wherein X9 is Ser.
6. The GRF analog of claim 1, wherein X11 is Arg.
7. The GRF analog of claim 1, wherein X12 is Lys or HoArg.
8. The GRF analog of claim 1, wherein X15 is Ala.
9. The GRF analog of claim 1, wherein X18 is Orn or Lys.
10. The GRF analog of claim 1, wherein X22 is Asp.
11. The GRF analog of claim 1, wherein X23 is Ile.
12. The GRF analog of claim 1, wherein X24 is Leu.
13. The GRF analog of claim 1, wherein X25 is Ala or Ser.
14. The GRF analog of claim 1, wherein X26 is Arg or D-Arg.
15. The GRF analog of claim 1, wherein X27 is Ala; X28 is Ala; X29 is Arg; X30 is Ala; X31 is Ala; X32 is Arg; and/or X33 is HoSer.
16. The GRF analog of claim 1, wherein at least one of X27 to X33 is absent.
17. The GRF analog of claim 16, wherein X27 to X33 are absent.
18. The GRF analog of claim 1, wherein said domain is:

(SEQ ID NO: 2)
Y-A-D-A-I-F-T-D-S-Y-R-K-V-L-A-Q-L-K-A-R-Q-D-I-L-A-R;

(SEQ ID NO: 3)
Y-a-D-A-I-F-T-D-S-Y-R-K-V-L-A-Q-L-K-A-R-Q-D-I-L-S-r;

(SEQ ID NO: 4)
Y-a-D-A-I-F-T-D-S-Y-R-K-V-L-A-Q-L-K-A-R-Q-D-I-L-aib-R;

(SEQ ID NO: 5)
Y-a-D-A-I-F-T-D-S-Y-R-K-V-L-A-Q-L-O-A-R-Q-D-I-L-S-r;

(SEQ ID NO: 6)
Y-A-D-A-I-F-T-D-S-Y-R-K-V-L-A-Q-L-O-A-R-Q-D-I-L-S-r;

(SEQ ID NO: 7)
Y-a-D-A-I-F-T-D-S-Y-R-K-V-L-A-Q-L-K-A-R-Q-D-L-L-S-r;

(SEQ ID NO: 8)
Y-A-D-A-I-F-T-D-S-Y-R-K-V-L-A-Q-L-K-A-R-Q-D-I-L-A-R-A-A-R;

(SEQ ID NO: 9)
Y-A-D-A-I-F-T-D-S-Y-R-K-V-L-A-Q-L-S-A-R-Q-D-I-L-A-R-A-A-R-A-A-R;

(SEQ ID NO: 10)
Y-a-D-A-I-F-T-D-S-Y-R-K-V-L-A-Q-L-K-A-R-Q-D-I-L-A-R-A-A-R-A-A-R;

```
                                    (SEQ ID NO: 11)
Y-a-D-A-I-F-T-D-S-Y-R-K-V-L-A-Q-L-K-L-R-Q-D-I-L-A-

R-A-A-R-A-A-R;

(SEQ ID NO: 12)
Y-a-D-A-I-F-T-D-S-Y-R-K-V-L-A-Q-L-K-A-R-Q-D-L-L-A-

R-A-A-R-A-A-R;

(SEQ ID NO: 13)
Y-A-D-A-I-F-T-D-S-Y-R-K-V-L-A-Q-L-K-A-R-Q-D-I-L-A-

R-A-A-R-A-A-R;

(SEQ ID NO: 14)
Y-A-D-A-I-F-T-D-S-Y-R-K-V-L-A-Q-L-K-A-R-Q-D-L-L-A-

R-A-A-R-A-A-R;

(SEQ ID NO: 15)
Y-S-D-A-I-F-T-D-S-Y-R-K-V-L-A-Q-L-K-A-R-Q-D-I-L-A-

R-A-A-R-A-A-R;

(SEQ ID NO: 16)
Y-G-D-A-I-F-T-D-S-Y-R-K-V-L-A-Q-L-K-A-R-Q-D-I-L-A-

R-A-A-R-A-A-R;

(SEQ ID NO: 17)
Y-L-D-A-I-F-T-D-S-Y-R-K-V-L-A-Q-L-K-A-R-Q-D-I-L-A-

R-A-A-R-A-A-R;

(SEQ ID NO: 18)
Y-G-D-A-I-F-T-D-S-Y-R-K-V-L-A-Q-L-K-A-R-Q-D-I-L-A-

R-A-A-R-A-A-R-HoSer;

(SEQ ID NO: 19)
Y-a-D-A-I-F-T-D-S-Y-R-K-V-L-A-Q-L-K-A-R-Q-D-I-L-A-

R-A-A-R-A-A-R-HoSer;

wherein a = D-Ala, O = L-Ornithine, Aib = α-amino-
isobutyric acid, HoSer = L-homoserine and r =
D-Arg.
```

19. The GRF analog of claim 1, further comprising (i) an amino-terminal modifying group; (ii) a carboxy-terminal modifying group; or (iii) both (i) and (ii).

20. The GRF analog of claim 19, wherein said amino-terminal modifying group is a trans-3-hexenoyl group.

21. The GRF analog of claim 19, wherein said carboxy-terminal modifying group is NH$_2$.

22. The GRF analog of claim 1, wherein said GRF analog is:

```
                                    (SEQ ID NO: 20)
Trans-3-hexenoyl-Y-A-D-A-I-F-T-D-S-Y-R-K-V-L-A-Q-

L-K-A-R-Q-D-I-L-A-R-NH2;

(SEQ ID NO: 21)
Y-a-D-A-I-F-T-D-S-Y-R-K-V-L-A-Q-L-K-A-R-Q-D-I-L-S- r-NH2;

(SEQ ID NO: 22)
Y-a-D-A-I-F-T-D-S-Y-R-K-V-L-A-Q-L-K-A-R-Q-D-I-L- aib-R-NH2;

(SEQ ID NO: 23)
Y-a-D-A-I-F-T-D-S-Y-R-K-V-L-A-Q-L-O-A-R-Q-D-I-L-S- r-NH2;

(SEQ ID NO: 24)
Trans-3-hexenoyl-Y-A-D-A-I-F-T-D-S-Y-R-K-V-L-A-Q-

L-O-A-R-Q-D-I-L-S-r-NH2;

(SEQ ID NO: 25)
Y-a-D-A-I-F-T-D-S-Y-R-K-V-L-A-Q-L-K-A-R-Q-D-L-L-S- r-NH2;

(SEQ ID NO: 26)
Trans-3-hexenoyl-Y-A-D-A-I-F-T-D-S-Y-R-K-V-L-A-Q-

L-K-A-R-Q-D-I-L-A-R-A-A-R-NH2;

(SEQ ID NO: 27)
Trans-3-hexenoyl-Y-A-D-A-I-F-T-D-S-Y-R-K-V-L-A-Q-

L-S-A-R-Q-D-I-L-A-R-A-A-R-A-A-R-NH2;

(SEQ ID NO: 28)
Y-a-D-A-I-F-T-D-S-Y-R-K-V-L-A-Q-L-K-A-R-Q-D-I-L-A-

R-A-A-R-A-A-R-NH2;

(SEQ ID NO: 29)
Y-a-D-A-I-F-T-D-S-Y-R-K-V-L-A-Q-L-K-L-R-Q-D-I-L-A-

R-A-A-R-A-A-R-NH2;

(SEQ ID NO: 30)
Y-a-D-A-I-F-T-D-S-Y-R-K-V-L-A-Q-L-K-A-R-Q-D-L-L-A-

R-A-A-R-A-A-R-NH2;

(SEQ ID NO: 31)
Trans-3-hexenoyl-Y-A-D-A-I-F-T-D-S-Y-R-K-V-L-A-Q-

L-K-A-R-Q-D-I-L-A-R-A-A-R-A-A-R-NH2;

(SEQ ID NO: 32)
Trans-3-hexenoyl-Y-A-D-A-I-F-T-D-S-Y-R-K-V-L-A-Q-

L-K-A-R-Q-D-L-L-A-R-A-A-R-A-A-R-NH2;

(SEQ ID NO: 33)
Y-S-D-A-I-F-T-D-S-Y-R-K-V-L-A-Q-L-K-A-R-Q-D-I-L-A-

R-A-A-R-A-A-R-NH2;

(SEQ ID NO: 34)
Y-G-D-A-I-F-T-D-S-Y-R-K-V-L-A-Q-L-K-A-R-Q-D-I-L-A-

R-A-A-R-A-A-R-NH2;

(SEQ ID NO: 35)
Y-L-D-A-I-F-T-D-S-Y-R-K-V-L-A-Q-L-K-A-R-Q-D-I-L-A-

R-A-A-R-A-A-R-NH2;

(SEQ ID NO: 36)
Y-G-D-A-I-F-T-D-S-Y-R-K-V-L-A-Q-L-K-A-R-Q-D-I-L-A-

R-A-A-R-A-A-R-HoSer-NH2;
or
                                    (SEQ ID NO: 37)
Y-a-D-A-I-F-T-D-S-Y-R-K-V-L-A-Q-L-K-A-R-Q-D-I-L-A-

R-A-A-R-A-A-R-HoSer-NH2;

wherein a = D-Ala, O = L-Ornithine, Aib = α-amino-
isobutyric acid, HoSer = L-homoserine and r =
D-Arg.
```

23. The GRF analog of claim 22, wherein said GRF analog is Y-a-D-A-I-F-T-D-S-Y-R-K-V-L-A-Q-L-K-A-R-Q-D-I-L-A-R-A-A-R-A-A-R-NH$_2$ (SEQ ID NO: 28); Y-a-D-A-I-F-T-D-S-Y-R-K-V-L-A-Q-L-K-L-R-Q-D-I-L-A-R-A-A-R-A-A-R-NH$_2$ (SEQ ID NO: 29); Y-a-D-A-I-F-T-D-S-Y-R-K-V-L-A-Q-L-K-A-R-Q-D-L-L-A-R-A-A-R-A-A-R-NH$_2$ (SEQ ID NO: 30); trans-3-hexenoyl-Y-A-D-A-I-F-T-D-S-Y-R-K-V-L-A-Q-L-K-A-R-Q-D-I-L-A-R-A-A-R-A-A-R-NH$_2$ (SEQ ID NO: 31); or trans-3-hexenoyl-Y-A-D-A-I-F-T-D-S-Y-R-K-V-L-A-Q-L-K-A-R-Q-D-L-L-A-R-A-A-R-A-A-R-NH$_2$ (SEQ ID NO: 32).

24. A pharmaceutical composition comprising the GRF analog of claim 1 and one or more pharmaceutically acceptable carriers, excipient, and/or diluents.

25. A method for inducing growth hormone secretion in a subject in need thereof, said method comprising administering to said subject an effective amount of the GRF analog of claim 1.

26. The method of claim 25, wherein said GRF analog is administered at a daily dose of about 0.1 mg to about 20 mg.

27. The method of claim 25, wherein said GRF analog is administered intravenously, orally, transdermally, subcutaneously, mucosally, intramuscularly, intranasally, intrapulmonary, parenterally, intrarectally or topically.

28. The method of claim 27, wherein said GRF analog is administered subcutaneously.

29. The method of claim 27, wherein said GRF analog is administered intranasally.

30. The method of claim 27, wherein said GRF analog is administered transdermally.

* * * * *

UNITED STATES PATENT AND TRADEMARK OFFICE
CERTIFICATE OF CORRECTION

PATENT NO. : 8,361,964 B2
APPLICATION NO. : 13/448660
DATED : January 29, 2013
INVENTOR(S) : Krishna G. Peri et al.

Page 1 of 1

It is certified that error appears in the above-identified patent and that said Letters Patent is hereby corrected as shown below:

At column 63, line 28 delete "H is;" and insert -- His; -- therefore.

At column 63, line 39, delete "Leu" and insert -- Leu; -- therefore.

Signed and Sealed this
Ninth Day of April, 2013

Teresa Stanek Rea
*Acting Director of the United States Patent and Trademark Office*